(12) United States Patent
Shimada et al.

(10) Patent No.: US 8,822,550 B2
(45) Date of Patent: Sep. 2, 2014

(54) TEMPERATURE-, PH- OR SALT CONCENTRATION-SENSITIVE SEPARATION MATERIAL AND USE THEREOF

(75) Inventors: Naohiko Shimada, Fukuoka (JP); Atsushi Maruyama, Fukuoka (JP)

(73) Assignee: Kyushu University, National University Corporation, Fukuoka-shi (JP)

( * ) Notice: Subject to any disclaimer, the term of this patent is extended or adjusted under 35 U.S.C. 154(b) by 0 days.

(21) Appl. No.: 13/636,436

(22) PCT Filed: Mar. 22, 2011

(86) PCT No.: PCT/JP2011/056844
§ 371 (c)(1),
(2), (4) Date: Sep. 21, 2012

(87) PCT Pub. No.: WO2011/118587
PCT Pub. Date: Sep. 29, 2011

(65) Prior Publication Data
US 2013/0012597 A1 Jan. 10, 2013

(30) Foreign Application Priority Data
Mar. 23, 2010 (JP) ................................. 2010-066792

(51) Int. Cl.
C08G 69/26 (2006.01)
C08F 26/02 (2006.01)
(52) U.S. Cl.
CPC ..................................... C08F 26/02 (2013.01)
USPC .......................... 514/772.3; 209/11; 435/180
(58) Field of Classification Search
CPC ............ C08F 26/02; C08F 8/30; C12N 11/08
USPC ........................... 514/772.3; 209/11; 435/180
See application file for complete search history.

(56) References Cited

U.S. PATENT DOCUMENTS

| 4,559,391 A | 12/1985 | Ueda |
| 2009/0087346 A1* | 4/2009 | Luchini et al. .................. 422/69 |

FOREIGN PATENT DOCUMENTS

| JP | S60-106803 | 6/1985 |
| JP | H04-110313 | 4/1992 |
| JP | H07-278235 | 10/1995 |
| JP | H10-204120 | 8/1998 |
| JP | H10-316827 | 12/1998 |

OTHER PUBLICATIONS

Stead et al., Title: Dyes and Pigments, vol. 3, pp. 161-171; published 1982.*

Buller et al.; Title: Tuning the lower critical solution temperature of thermoresponsive polymers by biospecific recognition; Polymer Chemistry, 2011, vol. 2, pp. 1486-1489.*
N. Shimada, et al.; "21) Polyallylamine Derivative Undergoing High-Temperature Soluble Phase Transition under Physiological Conditions;" The Society of Polymer Science; Japan Iyo Kobunshi Symposium Koen Yoshishu; Jul. 16, 2010; vol. 39; pp. 71-72.
T. Okano, et al; "A novel recovery system for cultured cells using plasma-treated polystyrene dishes grafted with ply(N-isopropylacrylamide);" Journal of Biomedical Materials Research; 1993; vol. 27; pp. 1243-1251.
Y. Kim, et al.; "pH/Temperature-sensitive polymers for macromolecular drug loading and release;" Journal of Controlled Release; 1994; vol. 28; pp. 143-152.
R. Buscall, et al.; "The Phase-Separation Behavior of Aqueous Solutions of Polyacrylic Acid and Its Partial Sodium Salts in the Presence of Sodium Chloride;" European Polymer Journal; 1982; vol. 18; pp. 967-974.
D. N. Schulz, et al.; "Phase behavior and solution properties of sulphobetaine polymers;" Polymer; 1986; vol. 27; pp. 1734-1742.
T. Aoki, et al.; "Adenosine-Induced Changes of the Phase Transition of Poly(6-(acryloyloxymethyl)uracil) Aqueous Solution;" Polymer Journal; 1999; vol. 31; No. 11-2; pp. 1185-1188.
S. Choi, et al.; "Active of DNA strand exchange by cationic comb-type copolymers: effect of cationic moieties of the copolymers;" Nucleic Acids Research; 2008; vol. 36; No. 1; pp. 342-351.
International Search Report issued for International Application No. PCT/JP2011/056844 dated Jun. 7, 2011.

* cited by examiner

*Primary Examiner* — Richard Schnizer
*Assistant Examiner* — Yanzhi Zhang
(74) *Attorney, Agent, or Firm* — Kratz, Quintos & Hanson, LLP

(57) ABSTRACT

The present invention provides a UCST-type thermoresponsive polymer compound which responds to a temperature under physiological conditions and has biofunctionality, and various uses thereof as a thermoresponsive material. Specifically, the invention provides a thermoresponsive material containing, as an active ingredient, a polymer compound represented by Formula (I) below or an addition salt thereof, the thermoresponsive material having an upper critical solution temperature in the range of 5 to 50° C. in an aqueous solution with a salt concentration of at least 1 mM and a pH in the range of 3 to 10.5:

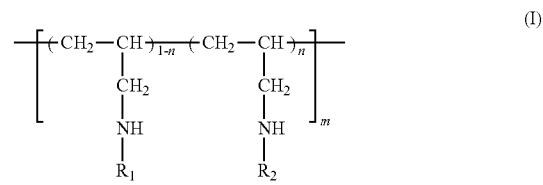

(I)

wherein m represents an integer of 10 or more; n represents a number satisfying $0.4 \leq n \leq 1$; $R_1$ represents hydrogen or succinyl; and $R_2$ represents carbamoyl.

10 Claims, 10 Drawing Sheets

(A)

(B)

Confocal image

Scale bar = 5μm (A)

(B)

TEMPERATURE-, PH- OR SALT CONCENTRATION-SENSITIVE SEPARATION MATERIAL AND USE THEREOF

TECHNICAL FIELD

The present invention relates to a temperature-, pH- or salt-concentration-sensitive separation material containing, as an active ingredient, a polymer compound or a salt thereof exhibiting a positive thermoresponsivity, which is insoluble in a low-temperature region and soluble in a high-temperature region under physiological conditions. The present invention also relates to the use of the separation material.

BACKGROUND ART

There have been many studies regarding low-temperature soluble (lower critical solution temperature-type: LCST-type) thermoresponsive polymer compounds in an aqueous solution. Due to the revelation of the phase-transition mechanism, molecular designing to control the phase transition temperature has also been clarified. For example, low-temperature soluble polymer compounds such as poly(N-isopropylacrylamide) are used as a basic material for cell sheet technology applicable to cell separation (Non-patent literature 1) or drug delivery systems (Non-patent literature 2), and serve as a trigger to bring new trends to regenerative medicine.

In contrast, even though the development of positive (upper critical solution temperature-type: UCST-type) thermoresponsive polymer compounds in an aqueous solution or under physiological conditions would result in basic materials that would greatly impact the engineering field, very few studies exist. This is because there are only a few examples of polymer compounds that exhibit UCST behavior in aqueous systems (Non-patent literature 3 to 5), and most of them do not exhibit thermoresponsive properties under physiological conditions, i.e., physiological pH, salt concentration and temperature.

CITATION LIST

Patent Literature

PTL 1: Japanese Unexamined Patent Publication No. 1985-106803

Non-Patent Literature

NPL 1: Okano, T. et al., (1993) J. Biomed. Mater. Res., 27, 1243-1251
NPL 2: Kim, Y.-H. et al., (1994) J. Control. Release, 28, 148-152
NPL 3: Buscall, R. et al., (1982) Eur. Polym. J., 18, 967-974
NPL 4: Schulz, D. N. et al. (1986) Polymer, 27, 1734-1742
NPL 5: Aoki, T. et al., (1999) Polymer. J., 31, 1185-1188

SUMMARY OF INVENTION

Technical Problem

For the reasons described above, the development of a high-temperature soluble polymer compound that is responsive under physiological conditions is essential. Therefore, the present invention provides a positive thermoresponsive polymer compound that is responsive under physiological conditions and has biofunctionality, and that also provides various applications thereof as a temperature-, pH- or salt-concentration-sensitive separation material.

Solution to Problem

The present inventors conducted intensive research and found that a polymer compound (H-PAA) having a hydrogen-bonding functional group attached to a specific proportion of side chains of polyallylamine represented by Formula (II) and a salt thereof exhibit high-temperature soluble (UCST-type) behavior.

wherein m represents an integer of 10 or more.

Specifically, under physiological conditions, i.e., physiological pH and salt concentration, they exhibit UCST-type behavior which are dissolved (dissolved phase) at a temperature higher than the predetermined temperature (phase transition temperature) and become insoluble (insoluble phase) by lowering the temperature below the phase transition temperature. The present inventors also found that the phase transition temperature can be suitably controlled by adjusting the pH or salt concentration, or by allowing an anionic substance or a cationic substance to coexist.

The present invention has been accomplished based on the above finding and includes the following embodiments.

(1) A Temperature-, pH- or Salt-Concentration-Sensitive Separation Material (1-1) A temperature-, pH- or salt-concentration-sensitive separation material (which hereunder may be referred to as a "thermoresponsive separation material") comprising, as an active ingredient, a polymer compound represented by Formula (I) or an addition salt thereof;

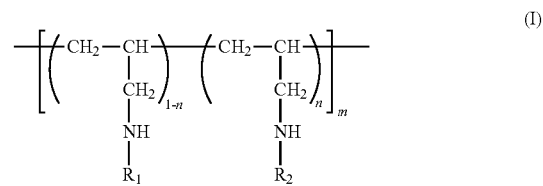

wherein m represents an integer of 10 or more, n represents a number satisfying $0.4 \leq n \leq 1$, $R_1$ represents hydrogen or a substituent represented by Formula (1), and $R_2$ represents a substituent represented by Formula (2):

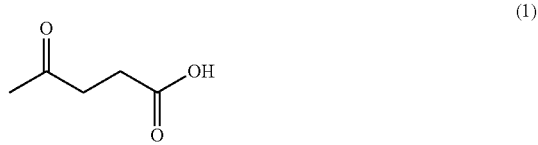

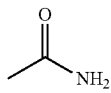
(2)

the polymer compound having a phase transition temperature in the range of 5 to 65° C. in an aqueous solution with a salt concentration of at least 1 mM and a pH in the range of 3 to 10.5; and forming an insoluble phase at a temperature lower than the phase transition temperature, and forming a dissolved phase at a temperature higher than the phase transition temperature.

(1-2) The thermoresponsive separation material described in (1-1) comprising a ligand binding, via a linker if necessary, to a part of the monomers constituting the thermoresponsive polymer compound (I).

(1-3) The thermoresponsive separation material described in (1-2), wherein the ligand is at least one member selected from the group consisting of biotin or imino biotin (or avidin or streptavidin), antibodies, sugar chains, lectins, protein A, protein G, DNA, RNA, enzymes, and receptors.

(1-4) The thermoresponsive separation material described in (1-2), wherein the ligand is biotin or imino biotin, and the linker is an alkylene group.

(1-5) The thermoresponsive separation material described in any one of (1-1) to (1-4), which further comprises an anionic substance or a cationic substance.

(1-6) The thermoresponsive separation material described in (1-5), wherein the anionic substance is an anionic dye.

(1-7) The thermoresponsive separation material described in (1-6), wherein the anionic dye is at least one member selected from the group consisting of fluorescein, bromophenol blue, trypan blue, and evans blue.

(2) Use of Thermoresponsive Separation Material (2-1) Use of the thermoresponsive separation material described in any one of (1-1) to (1-7) as a material for preparing a separating/concentrating agent, drug delivery system carrier, drug release matrix, enzyme immobilization matrix, antibody immobilization matrix, cell culture substrate, light modulator, optical functional material, or sensing substrate.

(2-2) A separating/concentrating agent, drug delivery system carrier, drug release matrix, enzyme immobilization matrix, antibody immobilization matrix, cell culture substrate, light modulator, optical functional material, or sensing substrate formed of the thermoresponsive separation material described in any one of (1-1) to (1-7) or comprising the thermoresponsive separation material as an active ingredient.

(2-3) A drug release agent comprising the thermoresponsive separation material described in any one of (1-1) to (1-7) in combination with a drug.

(2-4) A method for releasing a drug from a drug release agent comprising bringing the drug release agent described in (2-3) maintained under a temperature condition that is lower than the phase transition temperature of a thermoresponsive separation material to a temperature higher than the phase transition temperature in an aqueous solution with a salt concentration of at least 1 mM and a pH in the range of 3 to 10.5.

The method may be achieved by changing the temperature of the aqueous solution from one higher than the phase transition temperature of the thermoresponsive separation material to one lower than the phase transition temperature, or by changing the phase transition temperature of the thermoresponsive separation material from one lower than the temperature of the aqueous solution to one higher than the temperature thereof by adjusting the pH or salt concentration of the aqueous solution.

(2-5) An immobilized enzyme or antibody comprising an enzyme or antibody immobilized in the thermoresponsive separation material described in any one of (1-1) to (1-7), wherein the enzyme or the antibody binds, via a linker if necessary, to a part of the monomers constituting the thermoresponsive polymer compound represented by Formula (I) forming the separation material.

(2-6) An enzymatic reaction comprising reacting an enzyme with a substrate by bringing the immobilized enzyme described in (2-5) maintained under a temperature condition that is lower than the phase transition temperature of a thermoresponsive separation material to a temperature higher than the phase transition temperature in an aqueous solution containing a substrate with a salt concentration of at least 1 mM and a pH in the range of 3 to 10.5.

(2-7) An antigen-antibody reaction comprising reacting an antibody with an antigen by bringing the immobilized antibody described in (2-5) maintained under a temperature condition that is lower than the phase transition temperature of a thermoresponsive separation material to a temperature higher than the phase transition temperature in an aqueous solution containing an antigen with a salt concentration of at least 1 mM and a pH in the range of 3 to 10.5.

The methods of (2-6) and (2-7) may be achieved by changing the temperature of the aqueous solution from one lower than the phase transition temperature of the thermoresponsive separation material to one higher than the phase transition temperature, or by changing the phase transition temperature of the thermoresponsive separation material from one higher than the temperature of the aqueous solution to one lower than the temperature thereof by adjusting the pH or salt concentration of the aqueous solution.

(3) An Aqueous Two-Phase Partition Method (3-1) An aqueous two-phase partition method comprising the following steps:

(1) allowing a sample containing an object to be separated to coexist with the thermoresponsive separation material described in any one of (1-1) to (1-7) in an aqueous solution with a salt concentration of at least 1 mM and a pH in the range of 3 to 10.5, and (2) performing phase separation by adjusting the temperature of the aqueous solution from a temperature higher than the phase transition temperature of the thermoresponsive separation material to a temperature lower than the phase transition temperature.

Here, step (2) may be performed by changing the temperature of the aqueous solution from one higher than the phase transition temperature of the thermoresponsive separation material to one lower than the phase transition temperature, or by changing the temperature of the phase transition temperature of the thermoresponsive separation material from one lower than the temperature of the aqueous solution to one higher than the temperature thereof by adjusting the pH or salt concentration of the aqueous solution.

(3-2) The aqueous two-phase partition method according to (3-1), which further comprises step (3) or steps (3) and (4) below:

(3) separating a phase in which an object to be separated is distributed from a non-distribution phase using a phase separation step and collecting the separated phase, (4) collecting the object to be separated from the phase in which the object to be separated is distributed, which was separated by the above step.

(3-3) The aqueous two-phase partition method described in (3-1) or (3-2), wherein the object to be separated is at least one member selected from the group consisting of proteins, cells, anionic substances, cationic substances, hydrogen-bonding substances, and hydrophobic-bonding substances.

(3-4) The aqueous two-phase partition method described in (3-3), wherein the anionic substance is an anionic dye.

(3-5) The aqueous two-phase partition method described in (3-4), wherein the anionic dye is at least one member selected from the group consisting of fluorescein, bromophenol blue, trypan blue, and evans blue.

(3-6) The aqueous two-phase partition method described in (3-3), wherein the cationic substance is a cationic dye.

(3-7) The aqueous two-phase partition method described in (3-6), wherein the cationic dye is at least one member selected from the group consisting of ethidium bromide, propidium iodide, and tetrakis(1-methylpyridium-4-yl)porphyrin p-toluenesulfonate.

(3-8) The aqueous two-phase partition method described in (3-3), wherein the hydrogen-bonding substance is nucleic acid or a nucleic acid derivative.

(3-9) The aqueous two-phase partition method described in (3-8), wherein the hydrophobic-bonding substance is paclitaxel or a carbon nanotube.

(4) A Positive Thermoresponsive Polymer Compound and a Production Method Therefor (4-1) A method for producing polymer compound (I) described in Item (1-1) above, wherein $R_1$ is hydrogen and $R_2$ is carbamoyl, i.e., a polymer represented by Formula (IV) or an addition salt thereof:

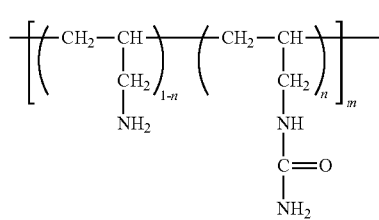

wherein m represents an integer of 10 or more, and n represents a number satisfying $0.4 \leq n \leq 1$, the method comprising reacting a cyanate with polyallylamine represented by Formula (II) or a partial salt thereof, the cyanate being used in a proportion of 67 to 100 mol %:

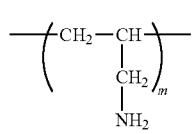

wherein m represents an integer of 10 or more.

(4-2) Succinylated carbamoylated polyallylamine represented by Formula (V) or an addition salt thereof:

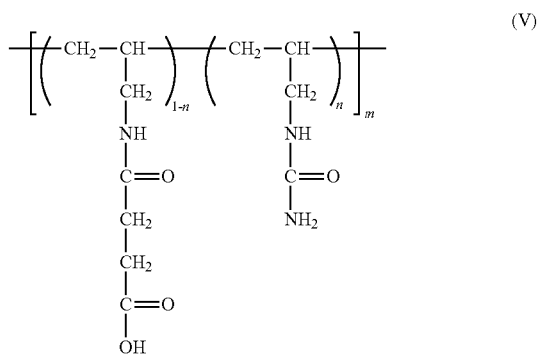

wherein m represents an integer of 10 or more, and n represents a number satisfying $0.4 \leq n \leq 1$.

(4-3) A method for producing the succinylated carbamoylated polyallylamine described in Item (4-2) represented by Formula (V) or an addition salt thereof comprising:

reacting a succinic anhydride with the carbamoylated polyallylamine represented by Formula (IV) or an addition salt thereof:

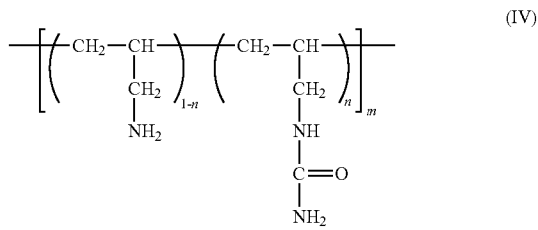

wherein m represents an integer of 10 or more, and n represents a number satisfying $0.4 \leq n \leq 1$.

Advantageous Effects of Invention

The positive thermoresponsive polymer compound (I) targeted by the present invention comprises a hydrogen-bonding functional group and a cationic functional group (amino group) at a specific proportion. While such polymer compound (I) does not exhibit a UCST-type thermoresponsive behavior in pure water, it exhibits a UCST-type thermoresponsive behavior in an aqueous solution with a salt concentration of at least 1 mM under physiological conditions. The polymer compound (I) has a property that forms a dissolved phase at a temperature higher than a specific temperature (phase transition temperature) and forms an insoluble phase at a temperature lower than the phase transition temperature.

By utilizing the thermoresponsive properties that are exhibited under physiological conditions, the thermoresponsive polymer compound (I) can be used as a separation material for capturing or separating various substances under physiological conditions. More specifically, the thermoresponsive polymer compound (I) can be effectively used, for example, for the separation of biochemical or physiological materials (e.g., physiologically active substances such as cells and proteins), DDS, drug release, enzyme immobilization, cell culturing, light modulation, and sensing. In particular, substances that are degenerated or subject to decreased activity under high-temperature conditions, and are therefore preferably not treated under high temperatures (e.g., cells, nucleic acids such as genes, proteins such as enzymes and antibodies, and other bioproducts), can be captured and separated (isolated) by using the thermoresponsive polymer compound (I) under temperature conditions lower than the phase transition temperature, without being degenerated or subject to decreased activity.

BRIEF DESCRIPTION OF DRAWINGS

FIG. 2 (B) shows the $^{13}$C-NMR spectra of the polyallylamine (PAA-15K) and the carbamoylated polyallylamine (Carb-PAA-15K 92; degree of carbamoylation: 0.92). The carbamoyl peak (O=O) is observed at 160 ppm.

FIG. 5 (B) shows the results of plotting the high-temperature soluble temperature UCST (° C.) (phase transition temperature) of 1 mg/ml, Carb-PAA-15K (Carb-PAA-15K 87 to 100), and the carbamoyl introduction rate (the degree of carbamoylation) on the horizontal axis.

FIG. 10 (B) shows the results of plotting the temperature of the mixtures on the horizontal axis, and the maximum absorption wavelength (nm) determined from the results of FIG. 10 (A) on the vertical axis.

FIG. 14 (upper) shows the relationship between the solution temperature (5 to 70° C.) and the transmittance (%) of the solution. FIG. 14 (lower) shows the relationship between the salt concentration and the phase transition temperature (° C.).

DESCRIPTION OF EMBODIMENTS

Figure 1:
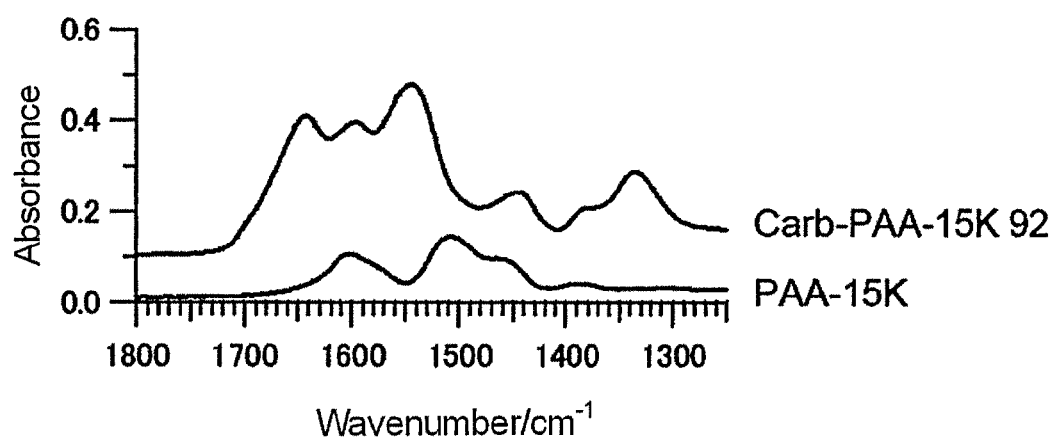
FIG. 1 shows the ATR-IR spectra (infrared absorption spectra) of polyallylamine (PAA-15K) and the carbamoylated polyallylamine (Carb-PAA-15K 92; degree of carbamoylation: 0.92) produced in Production Example 1.

1. Positive Thermoresponsive Polymer Compound and Production Method Therefor

The thermoresponsive polymer compound (I) used as an active ingredient of the temperature-, pH- or salt-concentration-sensitive separation material (hereinafter simply referred to as "thermoresponsive separation material") is represented by the following formula:

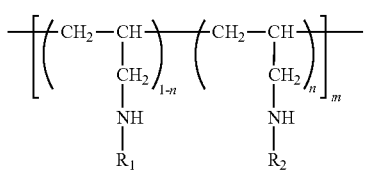
(I)

wherein m represents the degree of polymerization of the thermoresponsive polymer compound of the present invention. More specifically, m is an integer of 10 or more, preferably 10 to 5,000, more preferably 20 to 2,000, and particularly preferably 20 to 1,000.

In the formula, n represents the degree of introduction of hydrogen-bonding functional groups ($R_1$ and $R_2$) in the thermoresponsive polymer compound of the present invention. More specifically, n represents a number satisfying $0.4 \leq n \leq 1$. From the viewpoint of physiological conditions, n is more preferably a number satisfying and even more preferably $0.87 \leq n \leq 1$.

In the present invention, the substituent represented by $R_1$ is a group having a proton acceptor, such as a hydrogen atom or an oxo group (C=O). Specific examples of groups having a proton acceptor include a succinyl group (1) represented by the following formula:

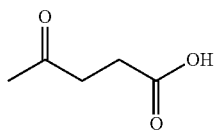
(1)

In the present invention, examples of the hydrogen-bonding functional group represented by $R_2$ include groups having a proton acceptor, such as an oxo group (C=O), and groups having a proton donor such as a primary amino group (—$NH_3$) or an imino group. Specific examples thereof include substituents (1'), (2), and (3') represented by the formulas below. A carbamoyl group represented by Formula (2) is preferable.

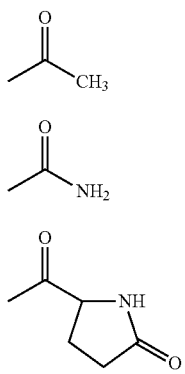
(1')

(2)

(3')

Examples of the addition salt of the thermoresponsive polymer compound (I) of the present invention include addition salts formed by addition to a side chain amino group of monomer units constituting the polymer compound. Examples of such addition salts include hydrochloride, hydrobromate, hydroiodide, sulphate, phosphate, phosphonate, acetate, and like carboxylates; methanesulfonate, p-toluenesulfonate, citrate, tartrate, and like oxycarboxylates; and benzoate.

Compound (III), which is a thermoresponsive polymer compound (I) of the present invention wherein $R_1$ is a hydrogen atom and $R_2$ is an acetyl group represented by Formula (1'), can be produced by reacting a polyallylamine represented by Formula (II) shown below or a salt thereof with acetic anhydride (($CH_3CO$)$_2$O). Examples of salts of polyallylamine (II) include inorganic salts such as hydrochloride, sulfate, and phosphate. The reaction between a polyallylamine or a salt thereof, and acetic anhydride is preferably performed by dissolving a polyallylamine or a salt thereof in water, an organic solvent, or a mixture thereof, then adding acetic anhydride dropwise and allowing the reaction to proceed while stirring.

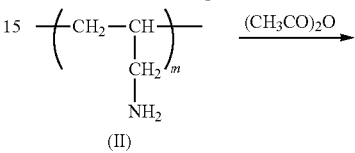
(II)

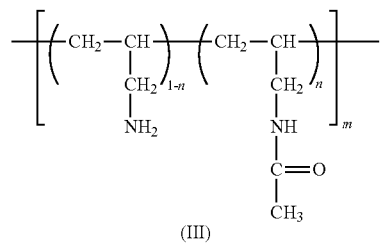
(III)

(wherein n and m are as defined above).

Acetic anhydride is used in an amount stoichiometrically required to introduce an acetyl group-containing substituent (1) into the polyallylamine (II) in a desired proportion (introduction rate) (n in Formula (III) is a number satisfying $0.4 \leq n \leq 1$).

Compound (IV), which is a thermoresponsive polymer compound (I) of the present invention wherein $R_1$ is a hydrogen atom and $R_2$ is a carbamoyl group represented by Formula (2), can be produced by reacting a polyallylamine represented by Formula (II) shown below or a salt thereof with a cyanate (MCNO). Examples of salts of polyallylamine (II) include inorganic salts, such as hydrochloride, sulfate, and phosphate.

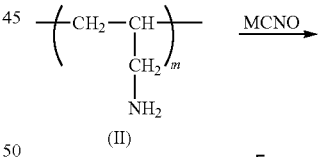
(II)

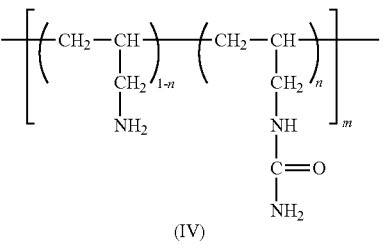
(IV)

(wherein n and m are as defined above, and MONO means a salt (M) of cyanic acid).

Methods for producing a polyallylamine (II) or a salt thereof are already well known. More specifically, for example, a polyallylamine (II) or a salt thereof can be produced according to Japanese Unexamined Patent Publication No. 1985-106803 (Patent Literature 1). A salt-free polyallylamine (II) can be produced by neutralizing a known polyallylamine salt with an alkali and then dialyzing the by-product neutralized salt with water. Commercially available (salt-free) polyallylamines are also usable. Examples of such commercially available products include a 15% polyallylamine (molecular weight: about 10,000) aqueous solution (PAA-15: produced by Nitto Boseki Co., Ltd.), a 10% polyallylamine (molecular weight: about 10,000) aqueous solution (PAA-10C: produced by Nitto Boseki Co., Ltd.), a 20% polyallylamine (molecular weight: about 10,000) aqueous solution (PAA-L: produced by Nitto Boseki Co., Ltd.), and a 20% polyallylamine (molecular weight: about 100,000) aqueous solution (PAA-H: produced by Nitto Boseki Co., Ltd.).

Examples of solvents used to form a polyallylamine (II) solution include water, organic solvents, and mixtures thereof. From the viewpoint of solubility of the polyallylamine, polar solvents are preferably used as organic solvents. Specific examples thereof include alcohols such as methanol, ethanol, 1-propanol, 2-propanol, and 1-butanol; acetonitrile, formamide, N,N-dimethylformamide, dimethyl sulfoxide, tetrahydrofuran, 1,4-dioxane, and the like. Although the concentration of polyallylamine in the polyallylamine solution used for the reaction is not particularly limited, it is typically 1 to 50 wt. %, preferably 2 to 30 wt. %, and more preferably 5 to 20 wt. %.

Preferable examples of cyanates (MONO) reacted with a polyallylamine (II) or a salt thereof include alkali metal salts of cyanic acid, such as potassium cyanate and sodium cyanate. Potassium cyanate is more preferable. Such a cyanate can be used in an amount stoichiometrically required to introduce a carbamoyl group-containing substituent (2) into the polyallylamine (II) in a desired proportion (introduction rate) (n in formula (IV) is a number satisfying $0.4 \le n \le 1$). More specifically, such a cyanate can be used in an amount of 0.4 to 10 mol per mol of the polyallylamine. The upper limit is not particularly limited insofar as it is 10 mol or less. The upper limit is preferably 5 mol or less, and more preferably 3 mol or less. The lower limit can be set to the number of mol corresponding to the introduction rate of the substituent (2) (degree of carbamoylation) (see Production Examples 1 and 2 and Tables 1 to 3. For example, to achieve a degree of carbamoylation of 0.4, the lower limit can be set to about 0.4 mol. To achieve a degree of carbamoylation of 0.8, the lower limit can be set to about 0.8.

When the polyallylamine (II) or salt thereof is reacted with a cyanate (MONO) to produce a polymer compound (IV) of the present invention wherein $R_1$ is a hydrogen atom and $R_2$ is a carbamoyl group, it is preferable that the cyanate (MONO) is slowly added dropwise to a solution of the starting polyallylamine (II) or salt thereof. At this time, the cyanate (MONO) may be dissolved in a solvent and the cyanate solution may be added to a solution of the starting polyallylamine (II) or salt thereof. In this case, the solvent used for dissolving the cyanate (III) is usually the same as the solvent used for dissolving the starting polyallylamine. The reaction between the polyallylamine (II) or salt thereof and the cyanate (MONO) is preferably performed while stirring. The reaction temperature is not particularly limited, but is preferably 0 to 100° C., and more preferably 30 to 60° C. The reaction time is not particularly limited, but is typically 12 to 48 hours and preferably 12 to 25 hours. A solution of the thermoresponsive polymer compound (IV) of the present invention can thus be obtained.

After completion of the reaction, the reaction solution is dried under a vacuum to remove the by-product alcohol and reaction solvent, thus obtaining a thermoresponsive polymer compound (IV) of the present invention as a solid.

The addition salt of the thermoresponsive polymer compound (IV) of the present invention can be produced by reacting a partial salt of polyallylamine as a starting material with a cyanate (MONO) and allowing these compounds to react in the same manner as using free polyallylamine. When a partial salt of polyallylamine as a starting material is reacted with a cyanate (III), a non-salt form of NH among the polyallylamine NH is preferentially substituted with a hydrogen-bonding substituent. After completion of the reaction, the obtained solution of the salt of thermoresponsive polymer compound (IV) is reprecipitated by adding a solvent, such as acetone, to obtain an addition salt of the thermoresponsive polymer compound (IV) of the present invention as a solid.

The thermoresponsive polymer compound (I) wherein $R_1$ is a hydrogen atom and $R_2$ is a pyroglutamyl group represented by (3') can be produced by introducing a pyroglutamyl group into an amino group of the polyallylamine (II) by an amide bond using pyroglutamic acid and a suitable condensing agent.

The degree of acetylation, degree of carbamoylation, and degree of pyroglutamylation (hereinafter sometimes collectively referred to as "the degree of acylation") (mol %) in the thermoresponsive polymer compound (I) of the present invention depends on the amount of acetic anhydride, cyanate, or pyroglutamic acid used as a starting material. When acetic anhydride, cyanate, or pyroglutamic acid is used in an equimolecular amount relative to the amino groups of the starting polyallylamine (II), most of the amino groups are usually acetylated, carbamoylated, or pyroglutamylated (acylated). Accordingly, adjusting the amount of acetic anhydride, cyanate, or pyroglutamic acid used as a starting material can adjust the cationic density of the thermoresponsive polymer compound of the present invention (or the density of the hydrogen-bonding substituent).

When $R_1$ is a hydrogen atom, the cationicity and hydrophobicity of the thermoresponsive polymer compound (I) of the present invention can be changed by the type of hydrogen-bonding substituent introduced as $R_2$. Accordingly, when the thermoresponsive polymer compound (I) of the present invention is used for various purposes, a hydrogen-bonding substituent having a suitable cationic density and suitable hydrophobicity is preferably selected.

The hydrogen-bonding substituent introduction rate (the production rate of the compound of the present invention), such as the degree of acylation of polyallylamine (II), can be determined by NMR measurement or colloid titration.

The thermoresponsive polymer compound (I) of the present invention can be a compound wherein $R_1$ is a succinyl group.

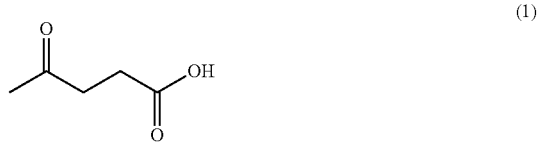

(1)

In this case, $R_2$ in Formula (I) is as defined above and is preferably a carbamoyl group represented by Formula (2).

Compound (V), which is a thermoresponsive polymer compound (I) of the present invention wherein $R_1$ is a succinyl group represented by the above Formula (1) and $R_2$ is a carbamoyl group represented by the above Formula (2), can be produced by reacting the thermoresponsive polymer compound of the present invention represented by Formula (IV) or a salt thereof, which is produced by the above-mentioned method, with succinic anhydride. Examples of the salt of the thermoresponsive polymer compound (IV) include inorganic salts, such as hydrochloride, sulfate, and phosphate.

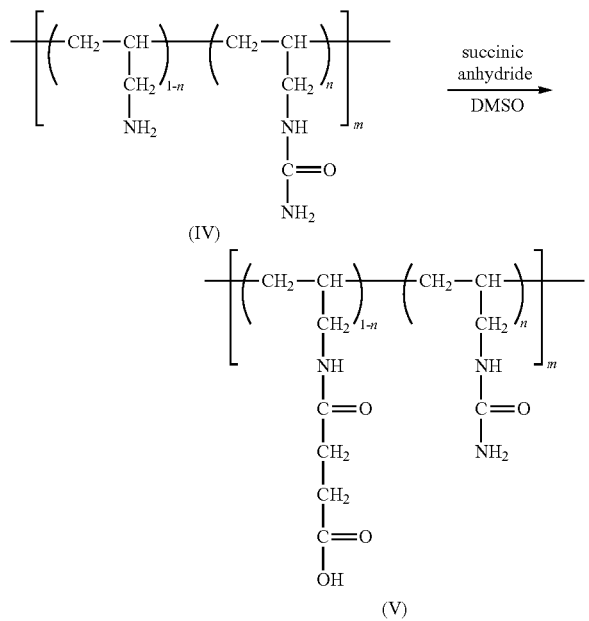

(wherein n and m are as defined above, and DMSO represents dimethyl sulfoxide.)

More specifically, the thermoresponsive polymer compound (IV) or a salt thereof is dissolved in DMSO. The thermoresponsive polymer compound (IV) or a salt thereof in the form of a solution is reacted with succinic acid, preferably with succinic anhydride. Succinic acid may be used, for example, in an amount stoichiometrically required to introduce a succinyl group (1) in a desired proportion (introduction rate) (n in Formula (V) is a number satisfying $0.4 \leq n \leq 1$). The succinic acid may be used in an amount of, for example, 1 to 5 equivalents, and preferably 3 equivalents or approximately 3 equivalents, relative to the primary amino group of the polymer compound (IV). The reaction temperature is not particularly limited, but is preferably maintained at 0 to 100° C., and more preferably 30 to 60° C. The reaction time is not particularly limited, but is typically 12 to 48 hours, and preferably 12 to 25 hours. A solution of the thermoresponsive polymer compound (V) of the present invention can thus be obtained.

After completion of the reaction, the reaction solution may be dialyzed to remove the unreacted product, by-product, and reaction solvent (DMSO). Thereafter, the dialysate may be dried under a vacuum to obtain a thermoresponsive polymer compound (V) of the present invention as a solid.

The addition salt of the thermoresponsive polymer compound (V) of the present invention can be produced by using an addition salt of the thermoresponsive polymer compound (IV) as a starting material.

A feature of the thus obtained thermoresponsive polymer compound (I) (including compounds (IV) and (V)) or addition salts thereof is to have a phase transition temperature in the range of 5 to 65° C., and preferably 5 to 50° C., in an aqueous solution with a salt concentration of at least 1 mM and a pH in the range of 3 to 10.5.

"To have a phase transition temperature in the range of 5 to 65° C. (or 5 to 50° C.)" means that the boundary temperature between the temperature at which the thermoresponsive polymer compound (I) or addition salt thereof is not dissolved in the above aqueous solution and forms an insoluble phase and the temperature at which the compound (I) or addition salt thereof is dissolved in the aqueous solution and forms a dissolved phase is in the range of 5 to 65° C. (or 5 to 50° C.). That is, the "phase transition" as used herein means a phase transition between the insoluble phase and dissolved phase formed of the thermoresponsive polymer compound (I) or salt thereof in the aqueous solution.

The "phase transition temperature" can be determined in the following manner. The thermoresponsive polymer compound (I) or addition salt thereof is dissolved in an aqueous solution with a salt concentration of at least 1 mM. While lowering the temperature, the transmission rate of 500 nm visible light is measured in a quartz cell. With the visible light transmission rate of a clear solution in which the compound is completely dissolved being defined as 100%, the temperature at which the transmission rate starts to be reduced is determined while lowering the temperature, and is defined as the phase transition temperature.

Examples of salts include KCl, NaCl, $CaCl_2$, $MgCl_2$, KBr, NaBr, $Na_2SO_4$, $MgSO_4$, and the like. When the thermoresponsive polymer compound (I) is a carbamoylated polyallylamine (Carb-PAA) represented by Formula (IV), sodium chloride is preferably used. When the thermoresponsive polymer compound (I) is a succinylated carbamoyl polyallylamine (Suc-Carb-PAA) represented by Formula (V), calcium chloride is preferably used.

2. Temperature-, pH-, or Salt-Concentration-Sensitive Separation Material

The temperature-, pH-, or salt-concentration-sensitive separation material (hereinafter simply referred to as the "thermoresponsive separation material") contains, as an active ingredient, the aforementioned thermoresponsive polymer compound (I) (including compounds (IV) and (V)) or addition salt thereof. Based on the characteristics of the active ingredient, the thermoresponsive separation material is also characterized by having a phase transition temperature in the range of 5 to 65° C., and preferably 5 to 50° C., in an aqueous solution with a salt concentration of at least 1 mM and a pH of 3 to 10.5.

The phase transition temperature of the thermoresponsive separation material may vary according to the type of solvent used for dissolving the separation material, the salt concentration of the solvent, the pH, the concentration of the separation material in the solvent, and the presence of other components in the solvent (in particular, the presence of anionic substances, cationic substances, hydrogen-bonding substances, or hydrophobic bonding substances, and the amounts thereof). However, as described above, the thermoresponsive separation material of the present invention contains a thermoresponsive polymer compound (I) or a salt thereof; has a phase transition temperature in the range of 5 to 65° C., and preferably 5 to 50° C., in an aqueous solution with a sodium chloride concentration of at least 1 mM and a pH of 3 to 10.5; forms an insoluble phase at a temperature lower than the phase transition temperature; and forms a dissolved phase at a temperature higher than the phase transition temperature.

An example of such a material is a thermoresponsive separation material comprising compound (IV), which is a thermoresponsive polymer compound (1) as described above wherein $R_1$ is a hydrogen atom, $R_2$ is a carbamoyl group (2), and which has a carbamoyl introduction rate (degree of carbamoylation) of 0.4 (n=0.4) or more, and preferably 0.67 (n=0.67) or more, or an addition salt thereof.

For example, a preferable thermoresponsive separation material has a phase transition temperature in the range of 10 to 45° C. in an aqueous solution with a sodium chloride concentration of at least 10 mM and a pH of 4 to 9.5; forms an insoluble phase at a temperature lower than the phase transition temperature; and forms a dissolved phase at a temperature higher than the phase transition temperature. Such a thermoresponsive separation material may, for example, comprise compound (IV), which is a thermoresponsive polymer compound (1) as described above wherein $R_1$ is a hydrogen atom and $R_2$ is a carbamoyl group (2), and which has a carbamoyl introduction rate (degree of carbamoylation) of 0.87 (n=0.87) or more, or an addition salt thereof.

A more preferable thermoresponsive separation material has a phase transition temperature in the range of 20 to 40° C. in an aqueous solution with a sodium chloride concentration of at least 50 mM and a pH of 5.5 to 8.5; forms an insoluble phase at a temperature lower than the phase transition temperature; and forms a dissolved phase at a temperature higher than the phase transition temperature. A specific example thereof is a thermoresponsive separation material comprising compound (IV), which is a thermoresponsive polymer compound (1) as described above wherein $R_1$ is a hydrogen atom and $R_2$ is a carbamoyl group (2), and which has a carbamoyl introduction rate (degree of carbamoylation) of 0.94 (n=0.94) or more, or an addition salt thereof.

Another preferable thermoresponsive separation material has a phase transition temperature in the range of 5 to 30° C. in an aqueous solution with a sodium chloride concentration of at least 150 mM and a pH of 4.5 to 5; forms an insoluble phase at a temperature lower than the phase transition temperature; and forms a dissolved phase at a temperature higher than the phase transition temperature. Further, another preferable thermoresponsive separation material has a phase transition temperature in the range of 30 to 36° C. in an aqueous solution with a sodium chloride concentration of at least 150 mM and a pH of 7.5; forms an insoluble phase at a temperature lower than the phase transition temperature; and forms a dissolved phase at a temperature higher than the phase transition temperature. Yet further, another preferable thermoresponsive separation material has a phase transition temperature in the range of 5 to 15° C. in an aqueous solution with a sodium chloride concentration of at least 150 mM and a pH of 7.5; forms an insoluble phase at a temperature lower than the phase transition temperature; and forms a dissolved phase at a temperature higher than the phase transition temperature. A specific example thereof is a thermoresponsive separation material comprising compound (V), which is a thermoresponsive polymer compound (I) as described above wherein $R_1$ is a succinyl group (1) and $R_2$ is a carbamoyl group (2), and which preferably has a carbamoyl introduction rate (degree of carbamoylation) of 0.87 (n=0.87).

The "phase transition temperature" is determined in the following manner, as described above. The thermoresponsive separation material is dissolved in an aqueous solution with a salt concentration of at least 1 mM. While lowering the temperature, the transmission rate of 500 nm visible light is measured in a quartz cell. With the visible light transmission rate of a clear solution in which the separation material is completely dissolved being defined as 100%, the temperature at which the transmission rate starts to be reduced is determined while lowering the temperature, and is defined as the phase transition temperature.

Examples of salts include KCl, NaCl, $CaCl_2$, $MgCl_2$, KBr, NaBr, $Na_2SO_4$, and $MgSO_4$. When the thermoresponsive polymer compound (I) is a carbamoylated polyallylamine represented by Formula (IV), sodium chloride is preferably used. When the thermoresponsive polymer compound (I) is a succinylated carbamoyl polyallylamine represented by Formula (V), calcium chloride is preferably used.

The salt concentration is not particularly limited, insofar as it is 1 mM or more as described above. The salt concentration is preferably 1 to 3,000 mM, and more preferably 50 to 1,000 mM. The concentration of the thermoresponsive separation material in the aqueous solution is typically 0.1 mg/ml or more, more preferably 0.1 to 300 mg/ml, and even more preferably 0.1 to 100 mg/ml, in terms of the concentration of the thermoresponsive polymer compound (I).

The thermoresponsive separation material of the present invention may contain a thermoresponsive polymer compound (I) or addition salt itself as an active ingredient. Alternatively, a ligand capable of binding to an object to be separated may be immobilized on a monomer unit of the thermoresponsive polymer compound (I), optionally via a linker, such as an alkylene group, and such a thermoresponsive polymer compound (I) comprising a ligand, or a salt thereof, may be contained as the active ingredient.

Examples of such ligands include biotin or iminobiotin (or avidin or streptavidin), antibodies (or antigens), molecular chaperones, sugar chains, lectin, protein A, protein G, DNA, RNA, enzymes (or substrates in enzymatic reactions), receptors (or ligands for receptors) (agonists or antagonists)), competitive inhibitors, coenzymes, and the like.

The method for binding the ligand to the thermoresponsive polymer compound (I) is not limited. For example, when a protein, such as an antibody (or an antigen), an enzyme, or a receptor, is to be bound as a ligand, a method of forming a peptide bond between a carboxyl group of the protein and an amino group of the thermoresponsive polymer compound (I) can be used. Alternatively, a carboxyl group of the ligand may be esterified with N-hydroxysuccinimide (NHS) into an activated ester group, and subsequently, an amide bond can be formed with an amino group of the thermoresponsive polymer compound (I) to thereby bind the ligand to the thermoresponsive polymer compound (I) (see, for example, Experimental Example 6).

The linker is not particularly limited. However, as described above, preferable examples of linkers include lower alkylene groups having 1 to 6 carbon atoms, preferably 1 to 4 carbon atoms, and more preferably 1 to 3 carbon atoms.

The anionic substance used in combination with the thermoresponsive separation material is not particularly limited, insofar as the substance has an anionic group. Examples of anionic substances include anionic dyes such as fluorescein (FL) having a monovalent anion, bromophenol blue (BPB) having a bivalent anion, trypan blue (TB) and Evan's blue (EB) having a tetravalent anion.

The cationic substance used in combination with the thermoresponsive separation material is not particularly limited insofar as the substance has a cationic group. Examples of cationic substances include ethidium bromide having a monovalent cation, propidium iodide having a divalent cation, TMPyP (tetrakis(1-methylpyridinium-4-yl)porphyrin p-toluenesulfonate having a tetravalent cation, and the like.

The thermoresponsivity of the thermoresponsive separation material of the present invention is reversible. The thermoresponsivity is preferably maintained even with repeated changes between dissolution and insolubilization.

3. Use of the Temperature-, pH-, or Salt-Concentration-Sensitive Separation Material The thermoresponsive separation material of the present invention can be used for various purposes and applications that are capable of utilizing the above characteristics. For example, the thermoresponsive separation material can be used as a separating/concentrating agent in an aqueous two-phase partition method (see (3-1) below), a matrix in a drug release agent (a drug release matrix) (see (3-3) below), a carrier in a drug delivery system (a drug delivery system carrier), a support for immobilizing an enzyme or an antibody (see (3-2) below), a cell culture substrate, a light modulator (see Experimental Example 5), an optical functional material, and a sensing substrate.

For example, when the thermoresponsive separation material of the present invention is used as a cell culture substrate or a component thereof, the thermoresponsive separation material is set to a temperature lower than the phase transition temperature thereof so as to culture cells on the substrate in an insoluble phase, and then adjusted to a temperature higher than the phase transition temperature to form a dissolved state, thus collecting the cells by liquefying the substrate. For example, when the thermoresponsive separation material of the present invention is used as a substrate of a pH or salt concentration sensor (a sensing substrate), an in vivo reaction involving pH or salt concentration changes can be measured.

(3-1) Aqueous Two-Phase Partition Method

The aqueous two-phase partition method can be performed by using the thermoresponsive separation material of the present invention as a separating agent or a concentrating agent. More specifically, the aqueous two-phase partition method utilizes the difference in the affinity of the object to be separated to two layers, i.e., affinity to an aqueous layer and to a coacervate layer formed when the temperature of an aqueous solvent used for dissolving the thermoresponsive separation material of the present invention is set to a temperature lower than the phase transition temperature of the thermoresponsive separation material. A test sample containing an object to be separated (a test sample to be separated) is dissolved in an aqueous solvent in which the thermoresponsive separation material has been dissolved, at a temperature higher than the phase transition temperature of the thermoresponsive separation material. Subsequently, the temperature of the solution is reduced to a temperature lower than the phase transition temperature to form a coacervate layer and an aqueous layer. The object to be separated is distributed more to either the coacervate layer or the aqueous layer according to the difference in the affinity to these layers. Accordingly, the object to be separated is collected from the target substance-distributed layer. If desired, by repeating this operation, the recovery rate of the target substance can be increased.

The aqueous two-phase partition method is particularly well suited to use for separating and concentrating an object to be separated that exhibits affinity to the thermoresponsive separation material of the present invention that forms a coacervate layer.

More specifically, in the present invention, the aqueous two-phase partition method can be performed by allowing a sample containing an object to be separated (a test sample) and the thermoresponsive separation material of the present invention to coexist in an aqueous solution with a salt concentration of at least 1 mM and a pH of 3 to 10.5, subsequently lowering the temperature of the aqueous solution from a temperature higher than the phase transition temperature of the thermoresponsive separation material to a temperature lower than the phase transition temperature. The object to be separated that has affinity to the thermoresponsive separation material of the present invention can be distributed to the coacervate layer formed of the thermoresponsive separation material. Accordingly, the object to be separated can be separated from the test sample by sedimentation of the coacervate layer using centrifugation or by concentration thereof using dialysis, etc. Examples of the salt include, but are not limited to, sodium chloride and calcium chloride. Other usable salts include KCl, NaCl, $MgCl_2$, KBr, NaBr, $Na_2SO_4$, $MgSO_4$, and the like.

When a thermoresponsive separation material containing a thermoresponsive polymer compound (IV) wherein $R_1$ is a hydrogen atom and $R_2$ is a carbamoyl group (2) or an addition salt thereof as an active ingredient is used, the object to be separated may be, for example, an anionic substance. The anionic substance is not particularly limited insofar as the substance has an anionic group. Specific examples thereof include anionic dyes, such as fluorescein (FL) having a monovalent anion, bromophenol blue (BPB) having a bivalent anion, trypan blue (TB) and Evan's blue (EB) having a tetravalent anion; and a cyanine anionic dye.

When a thermoresponsive separation material containing a thermoresponsive polymer compound (V) wherein $R_1$ is a succinyl group (1) and $R_2$ is a carbamoyl group (2) or an addition salt thereof as an active ingredient is used, the object to be separated may be, for example, a cationic substance. The cationic substance is not particularly limited insofar as the substance has a cationic group. Specific examples thereof include ethidium bromide having a monovalent cation, propidium iodide having a divalent cation, and TMPyP (tetrakis (1-methylpyridinium-4-yl)porphyrin p-toluenesulfonate having a tetravalent cation.

Other examples of the object to be separated include proteins, cells, hydrogen-bonding substances, hydrophobic bonding substances, and the like. Examples of hydrogen-bonding substances include nucleic acids such as RNA and DNA, nucleic acid derivatives such as antisense nucleic acids, siRNA, miRNA, ribozymes, and RNA aptamers. Examples of hydrophobic bonding substances include anti-cancer agents such as paclitaxel, and carbon nanotubes.

The thermoresponsive separation material used in the aqueous two-phase partition method may contain, as an active ingredient, a thermoresponsive polymer compound (I) or an addition salt thereof itself. Alternatively, a ligand capable of binding to an object to be separated may be immobilized on a monomer unit of the thermoresponsive polymer compound (I), optionally via a linker, such as an alkylene group, and such a thermoresponsive polymer compound (I) comprising a ligand, or a salt thereof, may be contained as the active ingredient.

Examples of such ligands include, as described above, biotin or iminobiotin (or avidin or streptavidin), antibodies (or antigens), molecular chaperones, sugar chains, lectin, protein A, protein G, DNA, RNA, enzymes (or substrates in enzymatic reactions), receptors (or ligands for receptors) (agonists or antagonists)), competitive inhibitors, coenzymes, and the like. Specific examples of pairs that are known to perform a specific interaction therebetween include antigen-antibody, enzyme-substrate (inhibitor), various types of bioactive substances-receptors, biotin or iminobiotin-avidin or streptavidin, DNA-DNA (RNA), and the like. Such a pair is not limited to a set of natural molecules but also includes a synthetic molecule-natural molecule set, and a synthetic molecule-synthetic molecule set. Examples of the interaction include electrostatic interactions, hydrophobic interactions, hydrogen bonding, and Van Der Waals interactions. Such interactions may be a single interaction or a combination thereof.

In the aqueous two-phase partition method of the present invention, a thermoresponsive separation material that has a phase transition temperature in a relatively low temperature range of preferably 5 to 36° C. can be used as a separating/concentrating agent. Accordingly, this method can be suitably used for bioseparation wherein the object to be separated is a bioproduct, such as a biomaterial of a microorganism or a cell culture; or a protein, such as an enzyme, an antibody, or a bioactive substance.

(3-2) Enzyme- or Antibody-Immobilization Matrix, and Reaction Method Using the Matrix The thermoresponsive separation material of the present invention can be used as an enzyme- and antibody-immobilization matrix (a solid phase). Immobilization of an enzyme or an antibody on the matrix can produce and provide an immobilized enzyme or an immobilized antibody.

Such an immobilized enzyme and immobilized antibody can be used as an effective material for the qualitative or quantitative analysis of a test substance (e.g., a protein) by immunoassay, etc., purification of a protein, and construction of a bioreactor. In this case, the thermoresponsive polymer compound (I) or salt thereof that is used preferably comprises a ligand capable of binding to an enzyme, the ligand being immobilized, via a linker if necessary, on a monomer unit of the thermoresponsive polymer compound (I). Examples of ligands that can be preferably used include biotin or iminobiotin as mentioned above.

The immobilized enzyme can be prepared by chemically immobilizing an enzyme on the thermoresponsive separation material (enzyme immobilization matrix) of the present invention. The method for immobilizing an enzyme may be the same as the method for binding a ligand (an enzyme) to the thermoresponsive polymer compound (I) as described in Section 2 above. The immobilized enzyme thus prepared is placed in an aqueous solution containing a substrate with a salt concentration of at least 1 mM and a pH of 3 to 10.5 and the temperature of the solution is set to be lower than the phase transition temperature of the thermoresponsive separation material, whereby the thermoresponsive separation material having the enzyme immobilized thereon (immobilized enzyme) is phase-separated as an insoluble phase. Then, a temperature higher than the phase transition temperature is achieved by changing the temperature, pH, etc., as desired to make the immobilized enzyme compatible with the aqueous solution containing the substrate, thus initiating an enzymatic reaction.

Further, the immobilized antibody can also be prepared by chemically immobilizing an antibody on the thermoresponsive separation material (antibody immobilization matrix) of the present invention. The method for immobilizing an antibody may be the same as the method for binding a ligand (an antibody) to the thermoresponsive polymer compound (I) described in Section 2 above. The immobilized antibody thus prepared is placed in an aqueous solution containing an antigen to the antibody with a salt concentration of at least 1 mM and a pH of 3 to 10.5 and the temperature of the solution is set to be lower than the phase transition temperature of the thermoresponsive separation material, whereby the thermoresponsive separation material having the antibody immobilized thereon (immobilized antibody) is phase-separated as an insoluble phase. Then, a temperature higher than the phase transition temperature is achieved by changing the temperature, pH, etc., as desired to make the immobilized antibody compatible with the aqueous solution containing the antigen, thus initiating an antigen-antibody reaction. Instead of the antibody, the antigen to the antibody may be immobilized on the thermoresponsive separation material, and an aqueous solution containing the antigen to the antibody may be prepared to perform an antigen-antibody reaction.

(3-3) Drug Release Agent and Drug Release Method

According to the present invention, a drug release agent can be provided by using the thermoresponsive separation material in combination with a drug. In the drug release agent, the thermoresponsive separation material of the present invention is used as a so-called drug delivery system (DDS) (a support for drugs). The drug release agent comprises the thermoresponsive separation material of the present invention and any desired drug. The drug release agent of the present invention exploits the properties of the thermoresponsive separation material of the present invention in order to control drug release and retention. More specifically, when the temperature is controlled under physiological conditions, the thermoresponsive separation material of the present invention is reversibly dissolved and insolubilized (undergoes phase transition), resulting in the dissolution and formation of coacervate. The drug release agent of the present invention can be suitably used as an intelligent drug delivery system (intelligent DDS) to administer a drug at a necessary time and in a necessary amount.

In the drug release agent of the present invention, the means for supporting or binding various drugs (for example, various anti-cancer drugs, such as Adriamycin and taxol) onto the thermoresponsive separation material of the present invention includes a method comprising bringing a desired drug into contact with the thermoresponsive separation material contained in an aqueous solution, while controlling the temperature, pH, etc., of the aqueous solution. More specifically, each of various drugs is allowed to coexist with the thermoresponsive separation material of the present invention in an aqueous solution with a salt concentration of at least 1 mM and a pH of 3 to 10.5, and the temperature, pH, etc., of the aqueous solution are controlled to lower the temperature of the solution below the phase transition temperature of the thermoresponsive separation material, whereby the drug can be supported on or bound to the thermoresponsive separation material of the present invention. Subsequently, the temperature, pH, etc. are controlled to raise the temperature above the phase transition temperature of the thermoresponsive separation material, whereby each of the drugs can be released from the thermoresponsive separation material of the drug release agent.

In this case, the thermoresponsive separation material may be a thermoresponsive polymer compound (I) or an addition salt thereof itself. Alternatively, a thermoresponsive polymer compound (I) comprising the aforementioned ligand immobilized thereon optionally via a linker, or an addition salt thereof may be used.

In the drug release agent of the present invention, the mode in which a drug is supported on or bound to the thermoresponsive separation material is preferably a method of binding a drug into or onto the surface of a coacervate layer formed of the thermoresponsive separation material by lowering the temperature below the phase transition temperature. The drug release agent of the present invention may further be subjected to a secondary treatment, i.e., the drug supported on or bound to the thermoresponsive separation material may be further enclosed in or supported on a substrate, such as a capsule, sponge, gel, or liposome. In this case also, the temperature is raised above the phase transition temperature of the thermoresponsive separation material by controlling the temperature, pH, etc., whereby each of various drugs can be released from a coacervate layer formed of the thermoresponsive separation material of the drug release agent.

The manner of administering the drug release agent of the present invention is also not particularly limited, and can be suitably selected according to the dosage form. For example, oral, transdermal, intravenous, intramuscular, or rectal administration can be selected according to the dosage form, such as an oral agent, a patch, an injection, a drip infusion, or a suppository.

The aqueous two-phase partition method, enzyme immobilization, drug release agent, etc., preferably use a bond utilizing an ion complex or charge transfer complex or a bond utilizing chemical affinity in order to bind a target substance or object to the thermoresponsive separation material of the present invention. The strength of binding of the target substance or object bound to the thermoresponsive separation material of the present invention can be controlled, for example, by one or a combination of the following methods: salt concentration control, pH control, control of inhibitor, substrate, etc., control of modifier such as urea and SDS, control of organic solvent, metal ion, etc., temperature control, and the like. This binding control further enables the control of the partition ratio, reaction rate, and drug release rate. To retain the repeatability of the thermoresponsive material, immobilization of various ligands onto the thermoresponsive material preferably uses a covalent bond. However, a bond utilizing an ion complex or charge-transfer complex or a bond utilizing biochemical affinity may also be used.

EXAMPLES

The structure and effects of the present invention are described in more detail below with reference to Production Examples and Experiment Examples. However, the present invention is not limited to these Production Examples and Experiment Examples.

Production Example 1

A polyallylamine hydrochloride (500 mg; 5 mmol as amine) was dissolved in 10 mL of water and heated to 50° C. A solution of potassium cyanate (260 mg to 1.3 g; about 0.6 to 3 mol per mol of polyallylamine dissolved in 1 mL of water was added dropwise thereto, and the resulting mixture was maintained at the same temperature for 24 hours. After completion of the reaction, dialysis against water was carried out using a dialysis membrane (MWCO: 3,500) at the same temperature for 24 hours to remove potassium chloride produced as a by-product, and freeze-drying was carried out. The polyallylamine hydrochloride used in this Production Example was one with a molecular weight of $1.5 \times 10^4$ (represented by Formula (II) wherein m is 150; hereinafter referred to as "PAA-15K").

FIG. 1 shows the ATR-IR spectra (infrared absorption spectra) of the polyallylamine (PAA-15K) used as a starting material and the polymer compound (carbamoylated polyallylamine: Carb-PAA92) obtained above. As is clear from the figure, the spectrum of the obtained polymer compound showed absorptions of carbamoyl groups at around 1,550 cm$^{-1}$ and 1,350 cm$^{-1}$.

Figure 2:
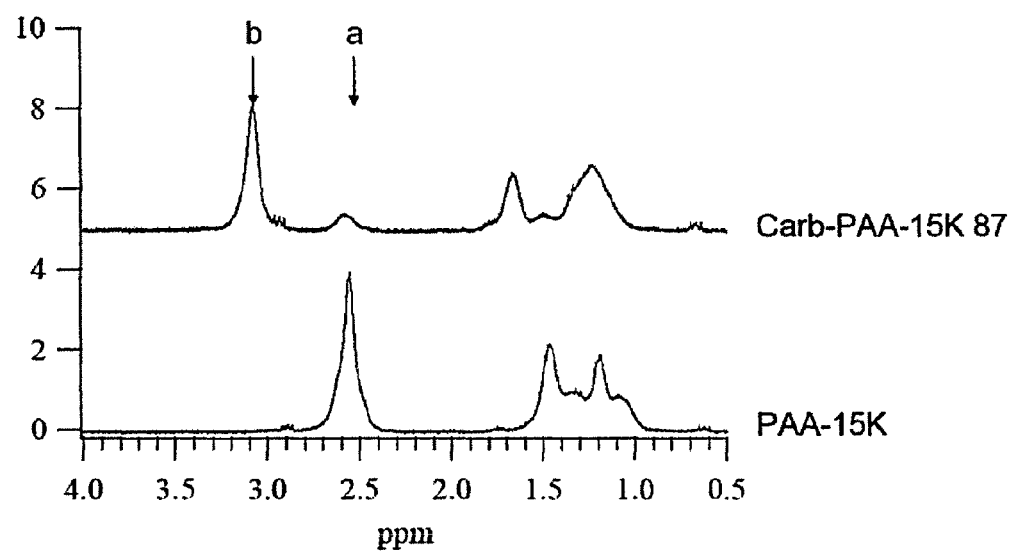
FIG. 2 (A) shows the $^1$H-NMR spectra of the polyallylamine (PAA-15K) and the carbamoylated polyallylamine (Carb-PAA-15K 87; degree of carbamoylation: 0.87). "a" indicates the proton peak of the uncarbamoylated methylene, and "b" indicates the proton peak of the carbamoylated methylene.
Figure 2:
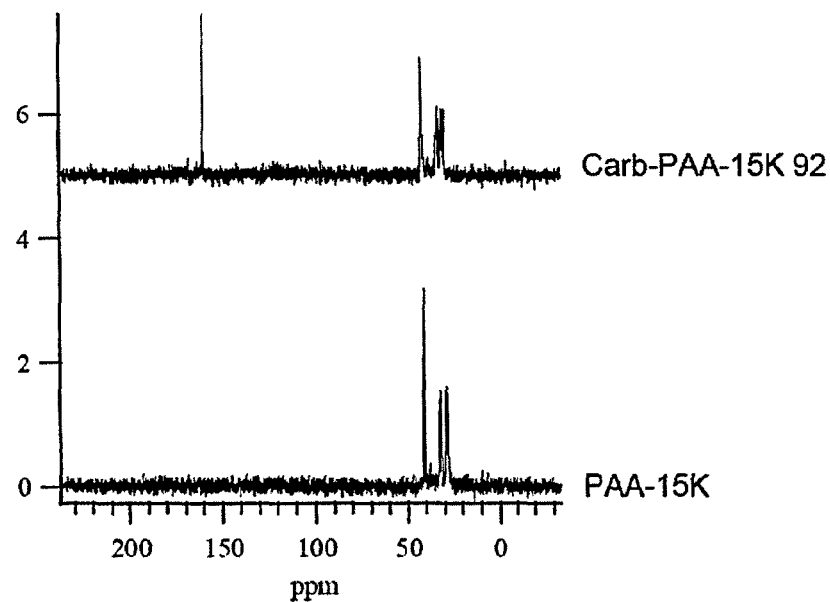

Then, 10 mg of the freeze-dried polymer compound (carbamoylated polyallylamine; hereinafter also referred to as "Carb-PAA-15K") (see Table 1) was added to heavy water containing 0.1% NaOD. NMR was measured at 60° C., and the carbamoyl introduction rate (the degree of carbamoylation) was determined. As an example of the NMR measurement data, FIG. 2 shows the NMR spectra of the polyallylamine (PAA-15K) and the carbamoylated polyallylamine (Carb-PAA-15K) (degree of carbamoylation: 0.87, Carb-PAA-15K 87). The degree of carbamoylation was calculated from the area ratio of the peaks at 2.6 ppm (the proton peak of the uncarbamoylated methylene: indicated by "a" in FIG. 2) and 3.1 ppm (the proton peak of the carbamoylated methylene: indicated by "b" in FIG. 2) according to the following formula:

$(b/(a+b)) \times 100\%$

Table 1 shows the results. Sample codes were assigned to samples based on the degree of carbamoylation.

TABLE 1

| Sample code | Amount of potassium cyanate (ratio per mol of polyallylamine) | Degree of carbamoylation |
| --- | --- | --- |
| Carb-PAA-15K (60) | 0.60 mol | 0.60 |
| Carb-PAA-15K (67) | 0.70 mol | 0.67 |
| Carb-PAA-15K (87) | 0.90 mol | 0.87 |
| Carb-PAA-15K (92) | 0.93 mol | 0.92 |
| Carb-PAA-15K (94) | 0.95 mol | 0.94 |
| Carb-PAA-15K (97) | 1.00 mol | 0.97 |
| Carb-PAA-15K (100) | 3.00 mol | 1.00 |

Production Example 2

The polyallylamine hydrochloride "PAA-15K" with a molecular weight of $1.5 \times 10^4$ was replaced by a polyallylamine hydrochloride with a molecular weight of $5 \times 10^3$ (represented by Formula (II) wherein m is 50; hereinafter also referred to as "PAA-5K") or a polyallylamine hydrochloride with a molecular weight of $1.5 \times 10^5$ (represented by Formula (II) wherein m is 1,500; hereinafter also referred to as "PAA-150K"). These polyallylamine hydrochlorides were each reacted with potassium cyanate at various ratios (see Tables 2 and 3) in the same manner as in Production Example 1, thereby producing carbamoylated polyallylamines (Carb-PAA 5K series and Carb-PAA 150K series). The degree of carbamoylation of each carbamoylated polyallylamine was determined by the method described in the Production Example.

TABLE 2

| Sample code | Amount of potassium cyanate (ratio per mol of polyallylamine) | Degree of carbamoylation |
| --- | --- | --- |
| Carb-PAA-5K (88) | 0.90 mol | 0.88 |
| Carb-PAA-5K (93) | 0.95 mol | 0.93 |
| Carb-PAA-5K (97) | 1 mol | 0.97 |
| Carb-PAA-5K (100) | 3 mol | 1.00 |

TABLE 3

| Sample code | Amount of potassium cyanate (ratio per mol of polyallylamine) | Degree of carbamoylation |
| --- | --- | --- |
| Carb-PAA-150K (83) | 0.85 mol | 0.83 |
| Carb-PAA-150K (89) | 0.9 mol | 0.9 |
| Carb-PAA-150K (93) | 0.95 mol | 0.93 |
| Carb-PAA-150K (96) | 1.00 mol | 0.96 |

Experiment Example 1

Carb-PAA-15K 92 prepared in Production Example 1 was dissolved in a biological buffer (10 mM Hepes-NaOH (pH 7.5)+150 mM NaCl in water) to a concentration of 2.5 mg/ml. Subsequently, the Carb-PAA-15K 92 solution was placed in a quartz cell, and the solution temperature was changed in the range of 5 to 70° C. The transmittance (%) of the solution during that period was measured by an ultraviolet-visible spectrophotometer. The transmittance (%) of the solution was calculated from the following formula:

$$\text{Transmittance}(\%)=10^{(-absorbance)}$$

Figure 3:
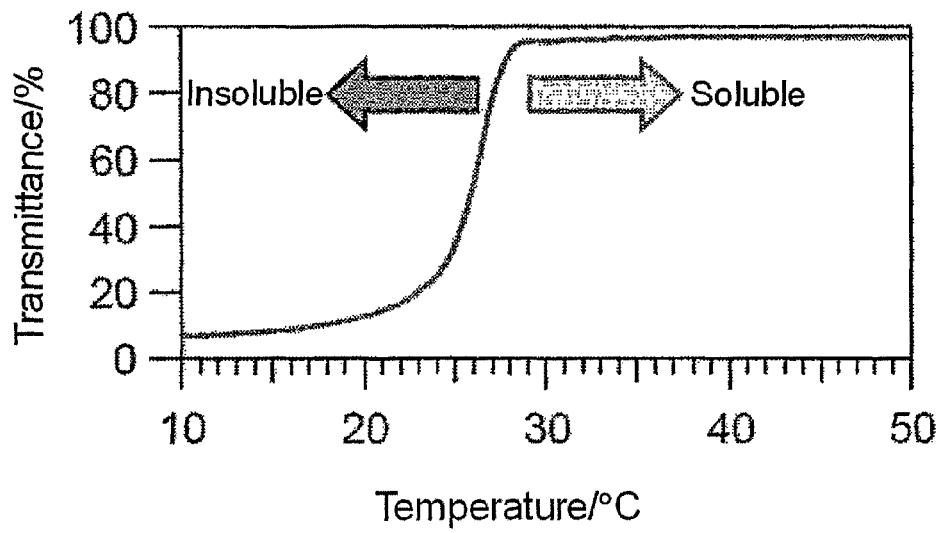
FIG. 3 shows the relationship between the temperature (° C.) and transmittance (%) of Carb-PAA-15K 92 (2.5 mg/ml) dissolved in a biological buffer (10 mM Hepes-NaOH (pH 7.5)+150 mM NaCl in water) (Experiment Example 1).

FIG. 3 shows the results. As is clear from FIG. 3, Carb-PAA-15K 92 was insoluble in the physiological aqueous solution with a low salt concentration in the temperature range lower than about 26° C. (phase transition temperature) and soluble in the temperature range higher than the phase transition temperature. That is, it was confirmed that Carb-PAA-15K 92 was a positive (upper critical solution temperature-type) thermoresponsive polymer compound. The phase transition was sharp and reversible.

Further, when the insoluble Carb-PAA-15K 92 under low-temperature conditions below 26° C. was centrifuged at 10,000 rpm for 3 minutes, Carb-PAA-15K 92 was precipitated. This indicates that the polymer compound of the present invention allows separation (bioseparation), capture, or concentration of substances that are deactivated or degenerated at high temperatures, such as biological materials (e.g., cells and proteins) and bioactive substances, while maintaining their activities under physiological low-temperature conditions. Moreover, since the polymer compound of the present invention is reversibly solubilized by increasing the temperature to exceed the above phase transition temperature, substances captured or concentrated under temperature conditions lower than that temperature can be separated and collected from the polymer compound by heating them to a temperature higher than the phase transition temperature. That is, the polymer compound of the present invention can be effectively used as a bioseparation material (a separating/concentrating agent).

Figure 4:
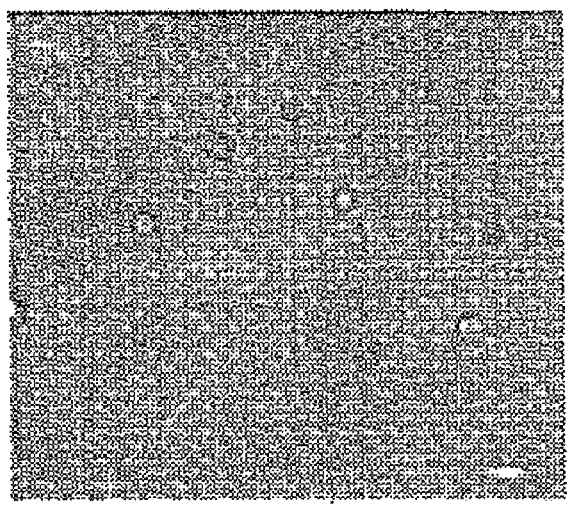
FIG. 4 shows a confocal image of a Carb-PAA-15K 92 solution (10 mM Hepes-NaOH (pH 7.5)+150 mM NaCl) with a concentration of 3.7 mg/mL observed by a confocal microscope under room temperature conditions (25° C.).

FIG. 4 shows a confocal image of the Carb-PAA-15K 92 solution (10 mM Hepes-NaOH (pH 7.5)+150 mM NaCl) with a concentration of 3.7 mg/mL observed by a confocal microscope under room temperature conditions (25° C.). As is clear from this image, Carb-PAA-15K 92 formed coacervates having a particle size of about 5 μm in the solution.

Experiment Example 2

Based on the results of Experiment Example 1, the phase transition temperatures of the various carbamoylated polyallylamines prepared in Production Examples 1 and 2 (Carb-PAA-15K, Carb-PAA-5K, and Carb-PAA-150K) were examined.

Specifically, the polyallylamines (PAA-15K, PAA-5K, and PAA-150K) used as starting materials and the various carbamoylated polyallylamines (Carb-PAA-15K (Carb-PAA-15K 87 to 100), Carb-PAA-5K, and Carb-PAA-150K) were each dissolved in a biological buffer (10 mM Hepes-NaOH (pH 7.5)+150 mM NaCl) to a concentration of 1 mg/ml. Subsequently, the resulting solution was placed in a quartz cell. While the solution temperature was reduced from 70° C. to 5° C. at a rate of 1° C./min, the absorbance at 500 nm was measured by a UV-VIS spectrophotometer (absorptiometer). The transmittance (%) was determined from the measured absorbance in the same manner as in Experiment Example 1.

Figure 5:
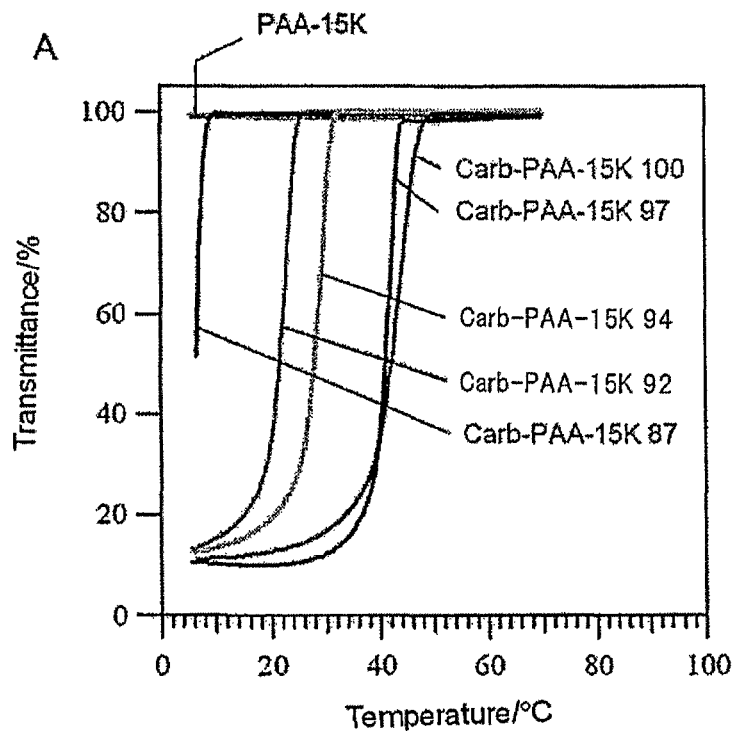
FIG. 5 (A) shows the transmittance % (500 nm) of biological buffers (10 mM Hepes-NaOH (pH 7.5)+150 mM NaCl) dissolving the polyallylamine (PAA-15K) and various Carb-PAA-15K (Carb-PAA-15K 87 to 100) (concentration: 1 mg/ml) in the temperature range of 5° C. to 70° C. (Experiment Example 2).
Figure 5:
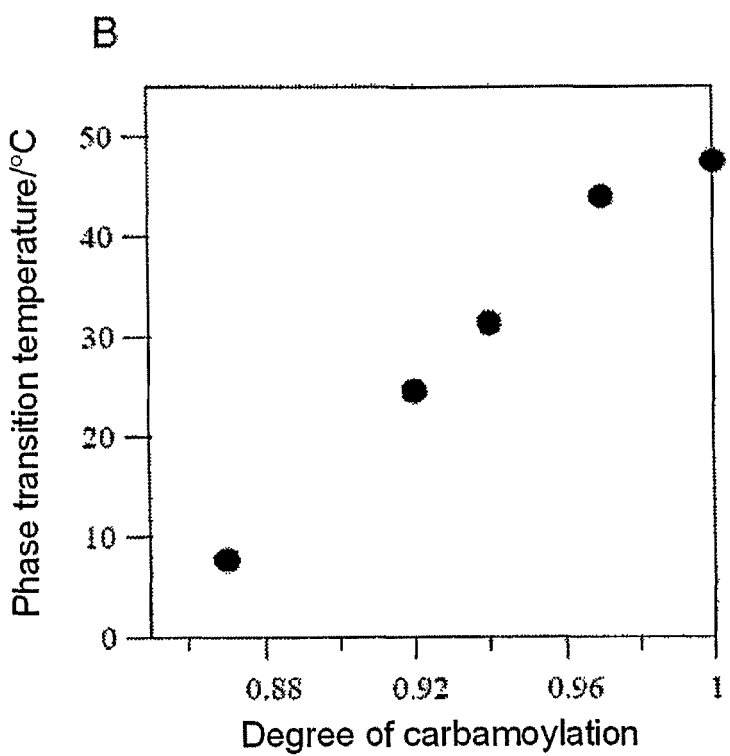

FIG. 5A shows the results of the polyallylamine (PAA-15K) and the carbamoylated polyallylamines (Carb-PAA-15K (Carb-PAA-15K 87 to 100)). As shown in FIG. 5A, it was confirmed that Carb-PAA 15K (1 mg/mL) having a degree of carbamoylation of 0.87 or more underwent sharp and reversible phase transition in the presence of the biological buffer (10 mM Hepes-NaOH (pH 7.5)+150 mM NaCl) in the temperature range of 5 to 50° C.

Table 4 shows the phase transition temperatures (° C.) of the various Carb-PAA-15K. As is clear from this table, Carb-PAA-15K (1 mg/mL) having a degree of carbamoylation of 0.87 or more were positive-polymer compounds having a phase transition temperature in the range of 5 to 50° C. under physiological conditions (10 mM Hepes-NaOH (pH 7.5)+150 mM NaCl).

In addition, Tables 5 and 6 show the phase transition temperatures (° C.) of various Carb-PAA-5K and Carb-PAA-150K. As is clear from these tables, Carb-PAA-5K (1 mg/mL) having a degree of carbamoylation of 0.88 or more were positive polymer compounds having a phase transition temperature in the range of 5 to 40° C. under physiological conditions (10 mM Hepes-NaOH (pH 7.5)+150 mM NaCl), and Carb-PAA-150K (1 mg/mL) having a degree of carbamoylation of 0.83 or more were positive polymer compounds having a phase transition temperature in the range of 5 to 67° C. under physiological conditions (10 mM Hepes-NaOH (pH 7.5)+150 mM NaCl).

TABLE 4

| Sample code | Degree of carbamoylation | Phase transition temperature (° C.) |
| --- | --- | --- |
| PAA-15K | 0.00 | >5 |
| Carb-PAA-15K 87 | 0.87 | 8 |
| Carb-PAA-15K 92 | 0.92 | 25 |
| Carb-PAA-15K 94 | 0.94 | 31 |
| Carb-PAA-15K 97 | 0.97 | 42 |
| Carb-PAA-15K 100 | 1.00 | 48 |

TABLE 5

| Sample code | Degree of carbamoylation | Phase transition temperature (° C.) |
| --- | --- | --- |
| PAA-15K | 0.00 | >5 |
| Carb-PAA-5K (88) | 0.88 | 8 |
| Carb-PAA-5K (93) | 0.93 | 25 |
| Carb-PAA-5K (97) | 0.97 | 33 |
| Carb-PAA-5K (100) | 1.00 | 40 |

TABLE 6

| Sample code | Degree of carbamoylation | Phase transition temperature (° C.) |
| --- | --- | --- |
| PAA-150K | 0.00 | >5 |
| Carb-PAA-150 (83) | 0.83 | 8 |
| Carb-PAA-150 (89) | 0.9 | 30 |
| Carb-PAA-150 (93) | 0.93 | 55 |
| Carb-PAA-150 (96) | 0.96 | 65 |

FIG. 5B shows the results of plotting the phase transition temperatures (° C.) of 1 mg/ml, Carb-PAA-15K (Carb-PAA-15K 87 to 100; indicated by black dots), and the carbamoyl introduction rate (the degree of carbamoylation) on the horizontal axis. Tables 4 to 6 and the results of FIG. 5B demonstrate that the phase transition temperature increased as the carbamoyl introduction rate (the degree of carbamoylation) increased in the presence of the biological buffer (10 mM Hepes-NaOH (pH 7.5)+150 mM NaCl) in the temperature range of 5 to 65° C. Furthermore, in the production of thermoresponsive polymer compounds with the desired phase transition temperature, the degree of carbamoylation can be determined on the basis of the correlation shown in FIG. 5B. For example, when producing thermoresponsive polymer compounds having a phase transition temperature of 15° C. by using the polyallylamine hydrochloride "PAA-15K" with a molecular weight of $1.5 \times 10^4$ as a starting material, the degree of carbamoylation may be set as 0.9.

Experiment Example 3

Regarding the various carbamoylated polyallylamines (Carb-PAA 15K) prepared in Production Example 1, the influences of Carb-PAA 15K concentration, pH, and salt concentration on the phase transition temperature were evaluated.

(1) Carb-PAA 15K Concentration Dependence

The phase transition temperature (° C.) was measured while the concentration of various Carb-PAA-15K (Carb-PAA-15K 87 to 100) was changed in the range of 0.1 to 5 mg/mL. More specifically, each of the various Carb-PAA-15K (Carb-PAA-15K 87 to 100) was dissolved in a biological buffer (10 mM Hepes-NaOH (pH 7.5)+150 mM NaCl) to a concentration of 0.1 to 5 mg/ml. While the solution temperature was reduced from 70° C. to 5° C. at a rate of 1° C./min, the absorbance at 500 nm was measured by a UV-VIS spectrophotometer (absorptiometer). The transmittance (%) was determined from the measured absorbance according to the method of Experiment Example 1. Based on the resulting transmittance of the various Carb-PAA-15K (Carb-PAA-15K 87 to 100) solutions in the concentration range of 0.1 to 5 mg/mL, the temperature at which the transmittance began to decrease, when the solutions were cooled from the state of 100% transmittance, was determined as the phase transition temperature.

Figure 6:
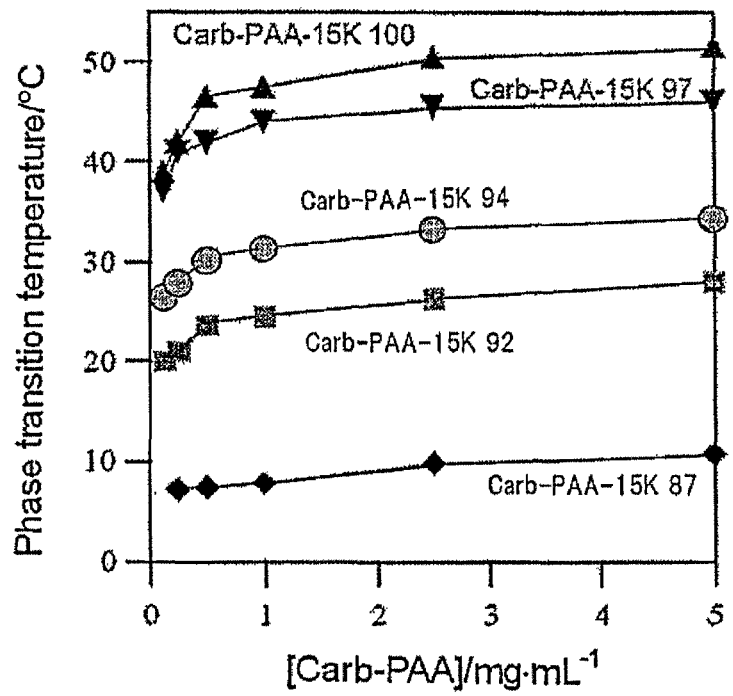
FIG. 6 shows the relationship between the Carb-PAA-15K concentration (0.1 to 5 mg/mL) and phase transition temperature ° C. (soluble temperature ° C.) of Carb-PAA-15K (Carb-PAA-15K 87 to 100) (Carb-PAA-15K concentration dependence). The horizontal axis represents the Carb-PAA-15K concentration (mg/mL), and the vertical axis represents the phase transition temperature (° C.).

FIG. 6 shows the results. In FIG. 6, the horizontal axis represents the Carb-PAA-15K concentration (mg/mL), and the vertical axis represents the phase transition temperature (° C.). The results reveal that the phase transition temperature of Carb-PAA 15K with a concentration of 0.1 to 5 mg/mL increased as the Carb-PAA-15K concentration increased in the presence of the biological buffer (10 mM Hepes-NaOH (pH 7.5)+150 mM NaCl).

From the results of FIG. 6, while varying the concentration of Carb-PAA-15K, when the temperature reaches a constant level at a certain concentration, this can prove that they are positive (UCST-type) thermoresponsive polymer compounds (thermoresponsive separation materials). Furthermore, the results of FIG. 6 demonstrate that thermoresponsive separation materials comprising the thermoresponsive polymer compound of the present invention as an active ingredient can adjust and control the phase transition temperature depending on the concentration of the polymer compounds.

(2) Evaluation of pH Dependence

The concentration of various Carb-PAA-15K (Carb-PAA-15K 67 and Carb-PAA-15K 87 to 97) was adjusted to 1 mg/ml, and the phase transition temperature (° C.) was measured while the pH was changed in the range of 5.5 to 10.5. More specifically, each of the various Carb-PAA-15K (Carb-PAA-15K 67 and Carb-PAA-15K 87 to 97) was dissolved in biological buffers, which had been adjusted to a pH of 5.5 to 10.5 (see the following), to a concentration of 1 mg/mL. While the solution temperature was reduced from 70° C. to 5° C. at a rate of 1° C./rain, the absorbance at 500 nm was measured by a UV-VIS spectrophotometer (absorptiometer). The phase transition temperature (° C.) was calculated from the measured absorbance according to the method of Experiment Example 2.

Figure 7:
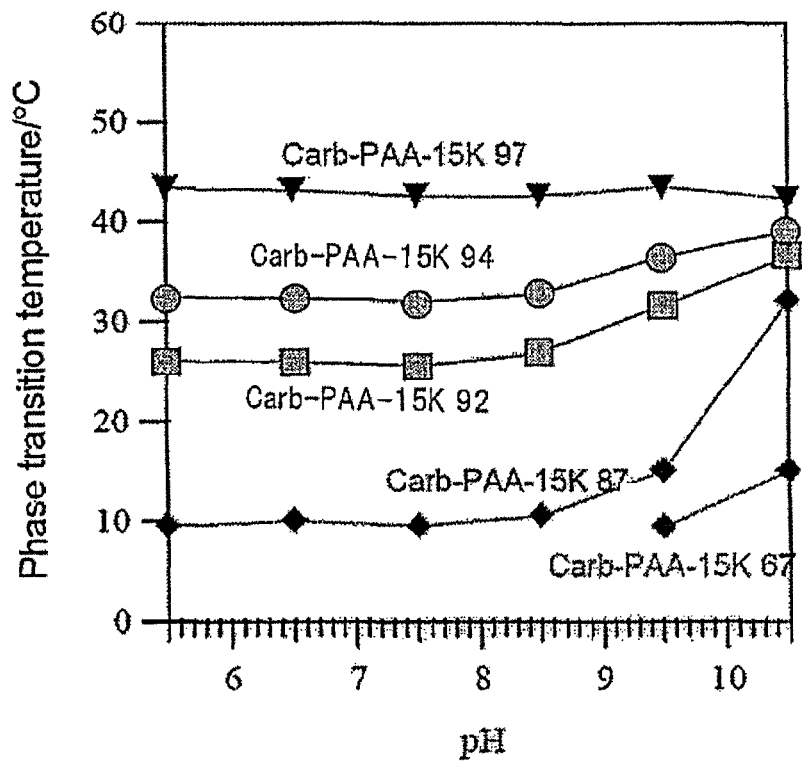
FIG. 7 shows the relationship between the pH and phase transition temperature ° C. (soluble temperature ° C.) of Carb-PAA-15K (Carb-PAA-15K 67 and 87 to 97; 1 mg/mL) (pH dependence). The horizontal axis represents the pH, and the vertical axis represents the phase transition temperature (° C.).

Buffers
pH 5.5 and 6.5: 10 mM MES-NaOH+150 mM NaCl
pH 7.5 and 8.5: 10 mM HEPES-NaOH+150 mM NaCl
pH 9.5 and 10.5: 10 mM boric acid-NaOH+150 mM NaCl FIG. 7 shows the results. In FIG. 7, the horizontal axis represents the pH of Carb-PAA-15K, and the vertical axis represents the phase transition temperature (° C.). As is clear from this figure, the phase transition temperatures (° C.) of any Carb-PAA-15K were almost constant in the pH range of 5.5 to 8.5, and showed no variation. As for Carb-PAA-15K 87 to 94, their phase transition temperatures (° C.) tended to increase in the pH range greater than 8.5 as the pH increased. This tendency was remarkable in Carb-PAA-15K 87, in which the carbamoyl introduction rate (the degree of carbamoylation) was relatively low. However, Carb-PAA-15K 97, in which the carbamoyl introduction rate (the degree of carbamoylation) was higher, maintained an almost constant phase transition temperature (° C.) in the pH range of 5.5 to 9.5. Furthermore, as shown in FIG. 7, it was confirmed that Carb-PAA-15K 67 was a positive thermoresponsive polymer compound having a phase transition temperature (° C.) in the range of 10 to 15° C. under alkaline conditions of pH 9.5 to 10.5.

The results demonstrate that even when, for example, the temperature of the system cannot be changed, the thermoresponsive separation material of the present invention can induce phase separation by changing the pH. Some sites in vivo undergo pH changes; in particular, for example, the vicinity of cancerous tissue is acidic. Accordingly, phase transition behavior presumably occurs depending on the pH environment of the tissue, and the thermoresponsive separation material of the present invention is expected to be usable for sensing.

(3) Evaluation of Salt Concentration Dependence

The phase transition temperature (° C.) was measured while the salt concentration of aqueous solutions dissolving various Carb-PAA-15K (Carb-PAA-15K 87 to 97) was changed in the range of 50 to 1,000 mM using 4N NaCl. More specifically, each of the various Carb-PAA 15K (Carb-PAA-15K 87 to 97) was dissolved in a buffer (10 mM HEPES-NaOH (pH 7.5)+50 to 1,000 mM NaCl), which had been adjusted to a salt concentration in the above range using 4N NaCl, to a concentration of 1 mg/mL. While the solution temperature was reduced from 70° C. to 5° C. at a rate of 1° C./min, the absorbance at 500 nm was measured by a UV-VIS spectrophotometer (absorptiometer). The phase transition temperature (° C.) was calculated from the measured absorbance according to the method of Experiment Example 2.

Figure 8:
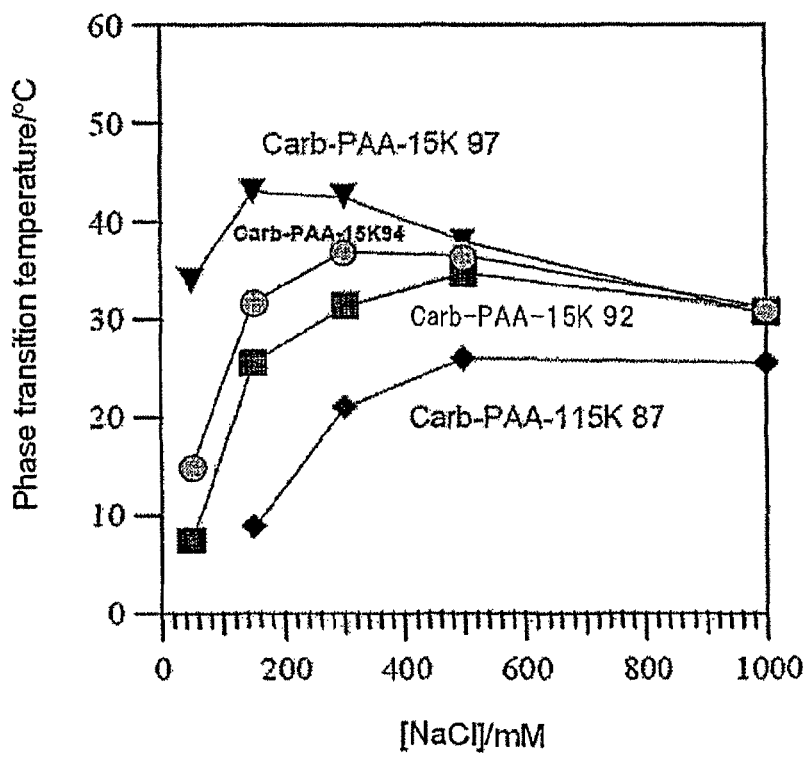
FIG. 8 shows the relationship between the salt concentration and phase transition temperature ° C. (soluble temperature ° C.) of Carb-PAA-15K (Carb-PAA-15K 87 to 97; 1 mg/mL) (salt concentration dependence). The horizontal axis represents the NaCl concentration (mM), and the vertical axis represents the phase transition temperature (° C.).

FIG. 8 shows the results. In FIG. 8, the horizontal axis represents the NaCl concentration (mM), and the vertical axis represents the phase transition temperature (° C.). As is clear from this figure, the phase transition temperatures (° C.) of Carb-PAA-15K 97, Carb-PAA-15K 94, and Carb-PAA-15K 87 and 92 tended to increase in the salt concentration range of 50 to 200 mM, 50 to 300 mM, and 50 to 400 mM, respectively, as the salt concentration increased. When the salt concentration was 1,000 mM (10 mM HEPES-NaOH (pH 7.5)+1,000 mM NaCl), the phase transition temperatures (° C.) of Carb-PAA-15K 92 to 97 were all 30° C., and the phase transition temperature (° C.) of Carb-PAA-15K 87 was 25° C. Further, the phase transition temperature (° C.) of Carb-PAA-15K 87 was maintained at about 25° C. in the salt concentration range of 500 to 1,000 mM.

In addition, none of Carb-PAA-15K underwent phase transition in a salt concentration of 0 mM, i.e., under pure water conditions. That is, it was confirmed that they were not positive thermoresponsive polymer compounds having a phase transition temperature.

The results reveal that even when, for example, the pH or temperature of the system cannot be changed, the thermoresponsive separation material of the present invention can induce phase separation by changing the salt concentration. For example, there is a method of allowing the thermoresponsive separation material of the present invention to capture an object to be separated under conditions of low salt concentration, and then adding a salt to the system to induce phase separation (separation).

Experiment Example 4

The influence of anionic substances on the phase transition temperature of Carb-PAA-15K was examined. The Carb-PAA-15K used was Carb-PAA-15K 87, and the anions used were anionic dyes (monovalent anion: fluorescein (FL); divalent anion: bromophenol blue (BPB); and tetravalent anions: trypan blue (TB) and evans blue (EB)).

More specifically, Carb-PAA-15K 87 was dissolved in a biological buffer (10 mM Hepes-NaOH (pH 7.5)+150 mM NaCl) to a concentration of 1 mg/mL. Each of the aforementioned anionic dyes was added thereto so that the concentration was 0 μM or 10 μM. While the solution temperature was reduced from 40° C. to 5° C. at a rate of 1° C./min, the transmittance (%) at 800 nm was measured by a UV-VIS spectrophotometer (absorptiometer).

Figure 9:
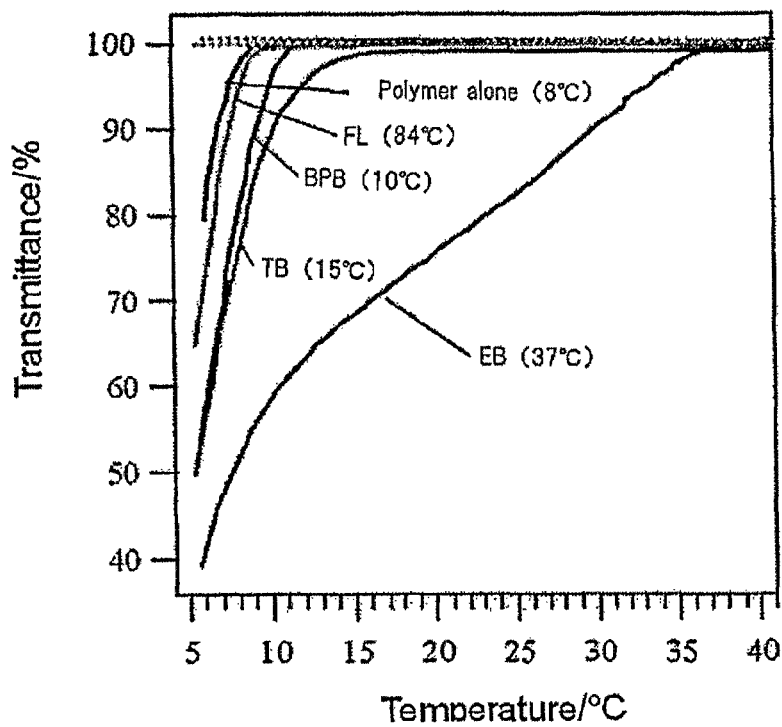
FIG. 9 shows the influence of anionic substances on the phase transition temperature of Carb-PAA-15K. The Carb-PAA-15K used was Carb-PAA-15K 87, and the anionic substances to be mixed therewith were anionic dyes (monovalent anion: fluorescein (FL); divalent anion: bromophenol blue (BPB); and tetravalent anions: trypan blue (TB) and evans blue (EB)). The horizontal axis represents the phase transition temperature (° C.), and the vertical axis represents the transmittance (%) at 800 nm. In the graph, the temperatures in parentheses indicate the phase transition temperatures (° C.) of mixtures of Carb-PAA-15K and the individual anionic dyes.

FIG. 9 shows the results. In FIG. 9, the horizontal axis represents the phase transition temperature (° C.), and the vertical axis represents the transmittance (%) at 800 nm. The results confirmed that the phase transition temperature of the polymer compound of the present invention varied in the presence of an anionic substance. It was also confirmed that the degree of the variation of the phase transition temperature depended on the number of anions, and that the more the number of anions, the higher the phase transition temperature. When there is an anionic substance targeted for capture, phase separation occurs upon addition of the thermoresponsive separation material of the present invention. Therefore, the anionic substance can be separated by centrifugation.

Experiment Example 5

The temperature of the mixtures (10 mM Hepes-NaOH (pH 7.5)+150 mM NaCl) of Carb-PAA-15K 87 and each of the various anionic dyes (monovalent anion: fluorescein (FL); divalent anion: bromophenol blue (BPB); and tetravalent anions: trypan blue (TB) and evans blue (EB)) prepared in Experiment Example 4 was adjusted to 10 to 50° C. The maximum absorption wavelength (nm) of the mixtures at each temperature was measured by a UV-VIS spectrophotometer (absorptiometer).

Figure 10:
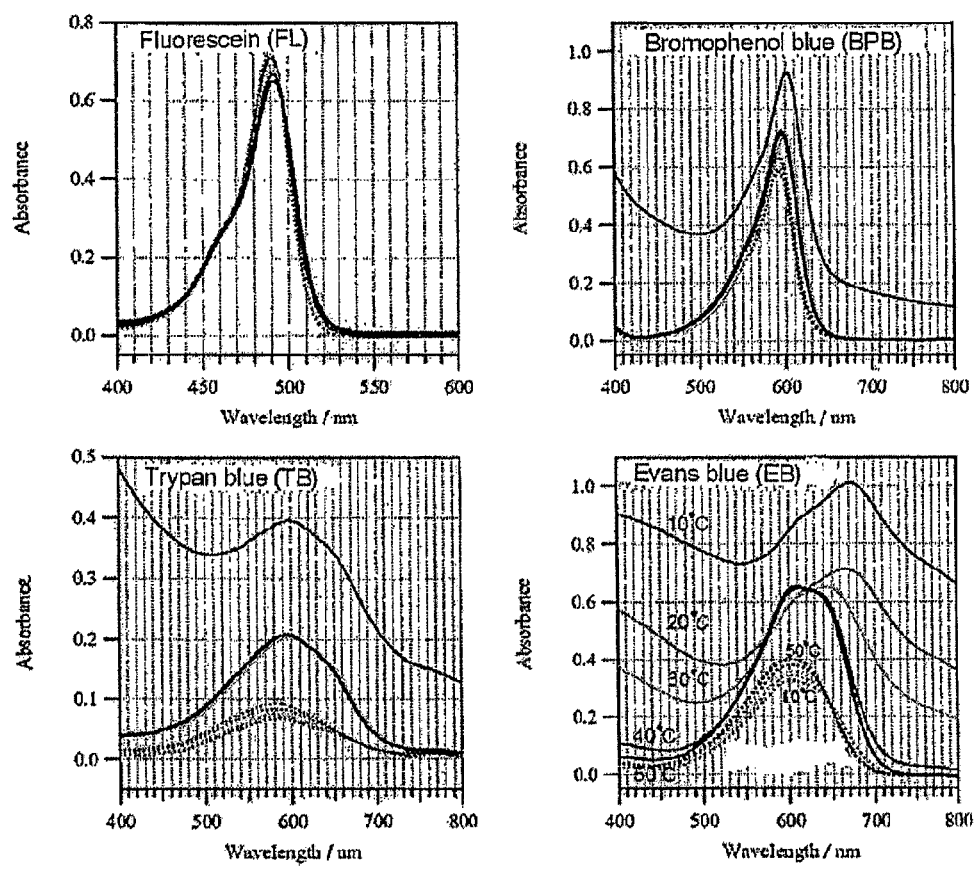
FIG. 10 (A) shows the maximum absorption wavelength (nm) of the mixtures (10 mM Hepes-NaOH (pH 7.5)+150 mM NaCl) of Carb-PAA-15K 87 and each of the various anionic dyes (monovalent anion: fluorescein (FL); divalent anion: bromophenol blue (BPB); and tetravalent anions: trypan blue (TB) and evans blue (EB)) prepared in Experiment Example 4. The temperature of the mixtures was adjusted to 10 to 50° C., and the maximum absorption wavelength (nm) of the mixtures at each temperature was measured by a UV-VIS spectrophotometer (absorptiometer).
Figure 10:
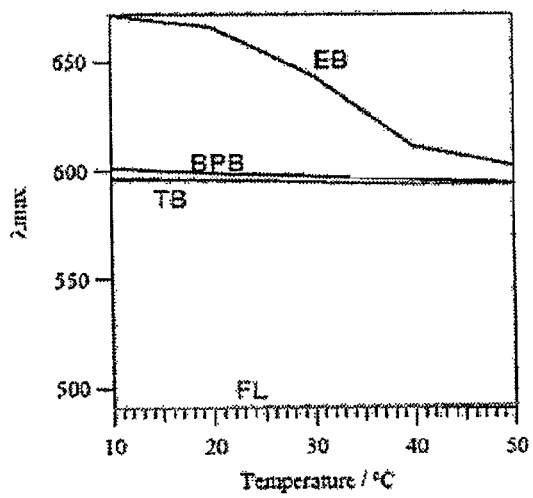

FIG. 10A shows the results. Further, FIG. 10B shows the results of plotting the temperature of the mixtures on the horizontal axis, and the maximum absorption wavelength (nm) determined from the results of FIG. 10A on the vertical axis.

As is clear from these figures, although the maximum absorption wavelength (nm) of evans blue (EB) alone did not vary depending on the temperature, the maximum absorption wavelength (nm) of Carb-PAA (87) mixed with evans blue (EB) varied depending on the temperature. That is, it was confirmed that the color tone of this mixture varied depending on the temperature (reversible variation). The temperature dependence of the maximum absorption wavelength (nm) was observed only in the mixture of Carb-PAA (87) and evans blue (EB), but was not observed in mixtures of Carb-PAA (87) and other anionic dyes (FIG. 10B).

The results reveal that the thermoresponsive separation material of the present invention is useful as a light modulator.

Experiment Example 6

Carb-PAA-15K 92 (50 mg) was dissolved in 3 mL of 0.1 M boric acid buffer (pH 9.0). Then, 2 ml of 0.1 M boric acid buffer (pH 9.0) mixed with biotin (0.4 mg), N-hydroxysuccinimide (3 mg), and 1-ethyl-3-(3-dimethylaminopropyl) carbodiimide (96 mg) was added thereto, and reacted at 30° C. for 2 hours. Moreover, 40 mg of polyallylamine hydrochloride was dissolved in 3 mL of 0.1 M boric acid buffer (pH 9.0). Then, 2 mL of 0.1 M boric acid buffer (pH 9.0) mixed with biotin (4 mg), N-hydroxysuccinimide (3 mg), and 1-ethyl-3-(3-dimethylaminopropyl) carbodiimide (96 mg) was added thereto, and reacted at 30° C. for 2 hours. Each of the above reaction solutions as dialyzed (MWCO: 3,500) against water and freeze-dried. $^1$H-NMR measurement revealed that the biotinylation rate of Carb-PAA 92 was 1 mol % (p=0.01, n=0.92) relative to the side chain. The biotinylation rate of polyallylamine was also 1 mol %.

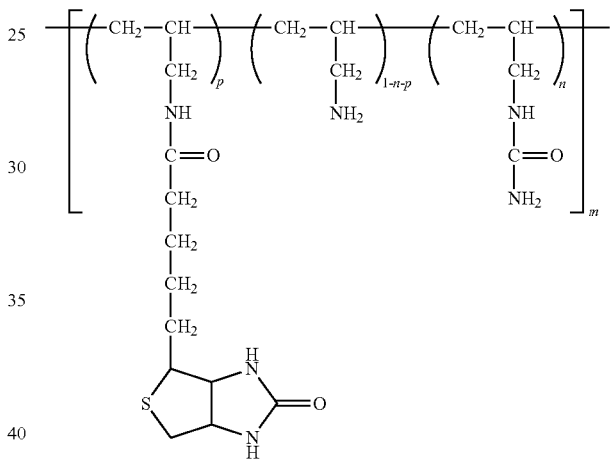

Figure 11:
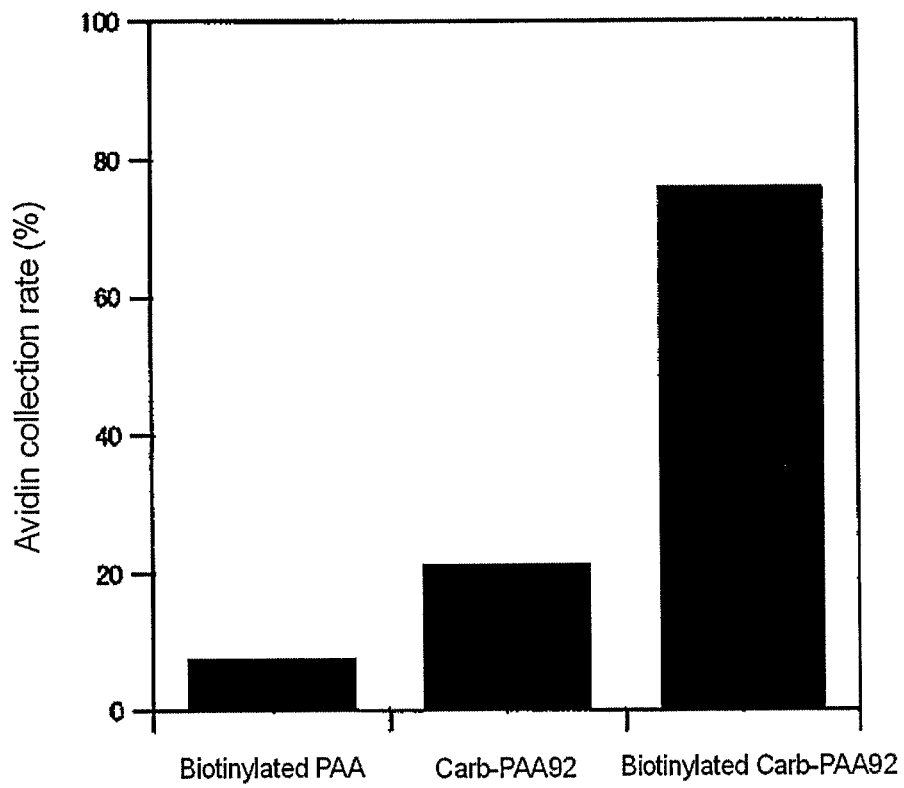
FIG. 11 shows a comparison of the avidin collection rates (%) when avidin was separated and collected by using, as a separation material, biotinylated PAA-15K obtained by biotinylating polyallylamine (PAA-15K), Carb-PAA-15K 92, and biotinylated Carb-PAA-15K 92 obtained by biotinylating Carb-PAA-15K 92 (Experiment Example 6).

The biotinylated Carb-PAA-15K 92 (2 mg) and rhodamine-marked avidin (5 μg) were suspended in 200 μl of buffer (10 mM HEPES-NaOH (pH 7.5)+50 to 1,000 mM NaCl), and incubated at 37° C. for 30 minutes. The result was then allowed to stand in ice for 10 minutes, and centrifuged at 4° C. at 10,000 rpm for 3 minutes. After the supernatant was removed, 200 μL of the above buffer was added and resuspended. Thereafter, fluorescence measurement (excitation wavelength: 545 nm, fluorescence wavelength: 575 nm) was performed to measure the amount of avidin collected. As control samples, Carb-PAA-15K 92 and the biotinylated polyallylamine (biotinylated PAA) were subjected to the same experiment as described above. FIG. 11 shows the results. The avidin collection rates of Carb-PAA-15K 92 and the biotinylated PAA were 25% or less, while the biotinylated Carb-PAA-15K 92 collected about 80% avidin. The results indicate that the polymer compound of the present invention was a material (bioseparator) capable of efficiently collecting protein at low temperature.

Production Example 3

The carbamoylated polyallylamine produced in Production Example 1 (100 mg; degree of carbamoylation: 0.87, Carb-PAA-15K 87) was dissolved in 5 mL of DMSO. Succinic anhydride was added in an amount of 3 equivalents per equivalent of the amino group of the carbamoylated polyallylamine (Carb-PAA-15K 87), and the mixture was reacted at 40° C. for 24 hours. After completion of the reaction, dialysis against water was carried out using a dialysis membrane (MWCO: 3,500) at the same temperature for 24 hours to remove by-products, and freeze-drying was performed.

Figure 12:
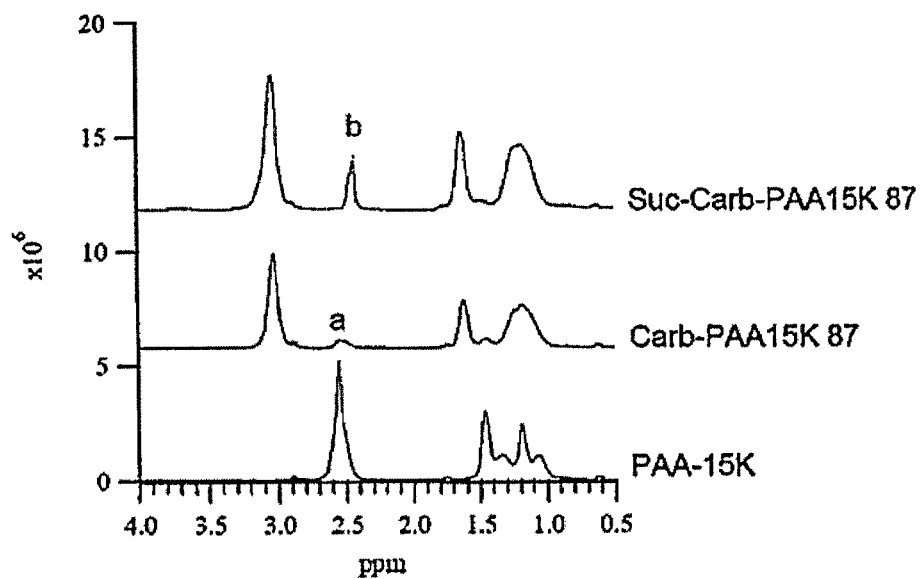
FIG. 12 shows the $^1$H-NMR spectra of the polyallylamine (PAA-15K), the carbamoylated polyallylamine (Carb-PAA-15K 87) (degree of carbamoylation: 0.87), and the succinylated carbamoylated polyallylamine (Suc-Carb-PAA-15K 87). "a" indicates the proton peak of the unsuccinylated methylene, and "b" indicates the proton peak of the ethylene derived from the succinyl group.

The freeze-dried polymer compound (10 mg; succinylated carbamoylated polyallylamine: hereinafter also referred to as "Suc-Carb-PAA-15K 87" or "succinylated CPA") was added to heavy water containing 0.1% NaOD. NMR was measured at 60° C., and the succinyl introduction rate (the degree of succinylation) was determined. As an example of the NMR measurement data, FIG. 12 shows the NMR spectra of the polyallylamine (PAA-15K), the carbamoylated polyallylamine (Carb-PAA-15K) (the degree of carbamoylation: 0.87, Carb-PAA-15K 87), and the succinylated carbamoylated polyallylamine (Suc-Carb-PAA-15K 87). From the fact that the peak "a" disappeared while a new peak "b" appeared, it was confirmed that all primary amino groups were succinylated.

Experiment Example 7

The succinylated carbamoylated polyallylamine (succinylated CPA) prepared in Production Example 3 was dissolved in a buffer (10 mM Hepes-NaOH (pH 7.5)+150 mM MgCl$_2$ or CaCl$_2$) to a concentration of 1 mg/ml. Subsequently, the succinylated CPA solution was placed in a quartz cell. While the solution temperature was changed from 70 to 5° C., the transmittance (%) of the solution during that period was measured by an ultraviolet visible spectrophotometer. The transmittance (%) of the solution was calculated from the following formula:

Transmittance(%)=$10^{(-absorbance)}$

Figure 13:
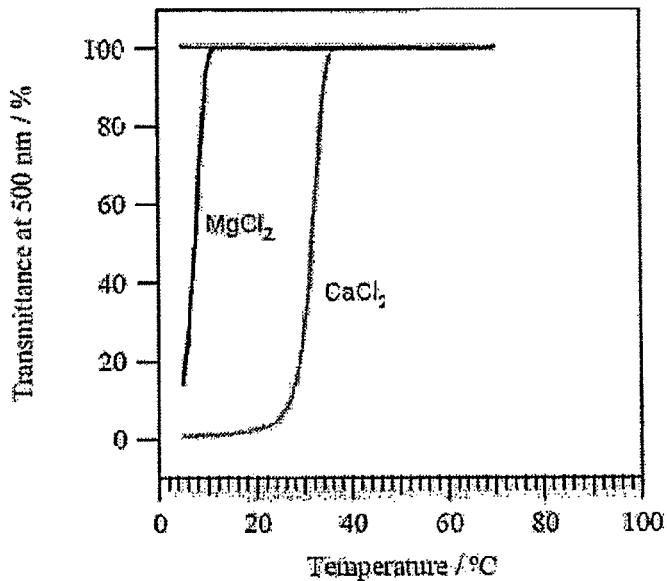
FIG. 13 shows the influence of salts (MaCl$_2$ and CaCl$_2$) on the phase transition temperature of the Suc-Carb-PAA-15K 87 prepared in Production Example 3 (Experiment Example 7). The horizontal axis represents the temperature (° C.), and the vertical axis represents the transmittance (%) at 500 nm.

FIG. 13 shows the results. As is clear from FIG. 13, the succinylated CPA was insoluble in the low-concentration MgCl$_2$ aqueous solution in the temperature range lower than about 10° C. (phase transition temperature) and soluble in the temperature range higher than the phase transition temperature. That is, it was confirmed that the succinylated CPA was a positive (upper critical solution temperature-type) thermoresponsive polymer compound. Moreover, the phase transition was sharp and reversible.

Furthermore, the succinylated CPA was insoluble in the low-concentration CaCl$_2$ aqueous solution in the temperature range lower than about 34.6° C. (phase transition temperature) and soluble in the temperature range higher than the phase transition temperature. That is, it was confirmed that the succinylated CPA was a positive (upper critical solution temperature-type) thermoresponsive polymer compound.

From the above results, the succinylated CPA allows, as with the above-mentioned carbamoylated polyallylamine, the separation (bioseparation), capture, or concentration of substances that are deactivated or degenerated at high temperatures, such as biological materials (e.g., cells and proteins) and bioactive substances, while maintaining their activities under physiological low-temperature conditions. Moreover, since the succinylated CPA of the present invention is reversibly solubilized by increasing the temperature to exceed the above phase transition temperature, substances captured or concentrated under temperature conditions lower than that temperature can be separated and collected from the succinylated CPA by heating them to a temperature greater than the phase transition temperature. That is, the succinylated CPA of the present invention can be effectively used as a bioseparation material (a separating/concentrating agent).

Experiment Example 8

Regarding the succinylated CPA prepared in Production Example 3, the influences of the salt concentration and pH on the phase transition temperature were evaluated.
(1) Evaluation of Salt Concentration Dependence Specifically, the phase transition temperature (° C.) was measured while the salt concentration (CaCl$_2$, Ca(NO$_3$)$_2$, CaBr$_2$) of a biological buffer (10 mM Hepes-NaOH, pH 7.5) dissolving the succinylated CPA was changed in the range of 50 to 1,000 mM. More specifically, the succinylated CPA was dissolved in the above biological buffer to a concentration of 1 mg/mL. While the solution temperature was reduced from 70° C. to 5° C. at a rate of 1° C./min, the absorbance at 500 nm was measured by a UV-VIS spectrophotometer (absorptiometer). The phase transition temperature (° C.) was calculated from the measured absorbance according to the method of Experiment Example 2.

Figure 14:
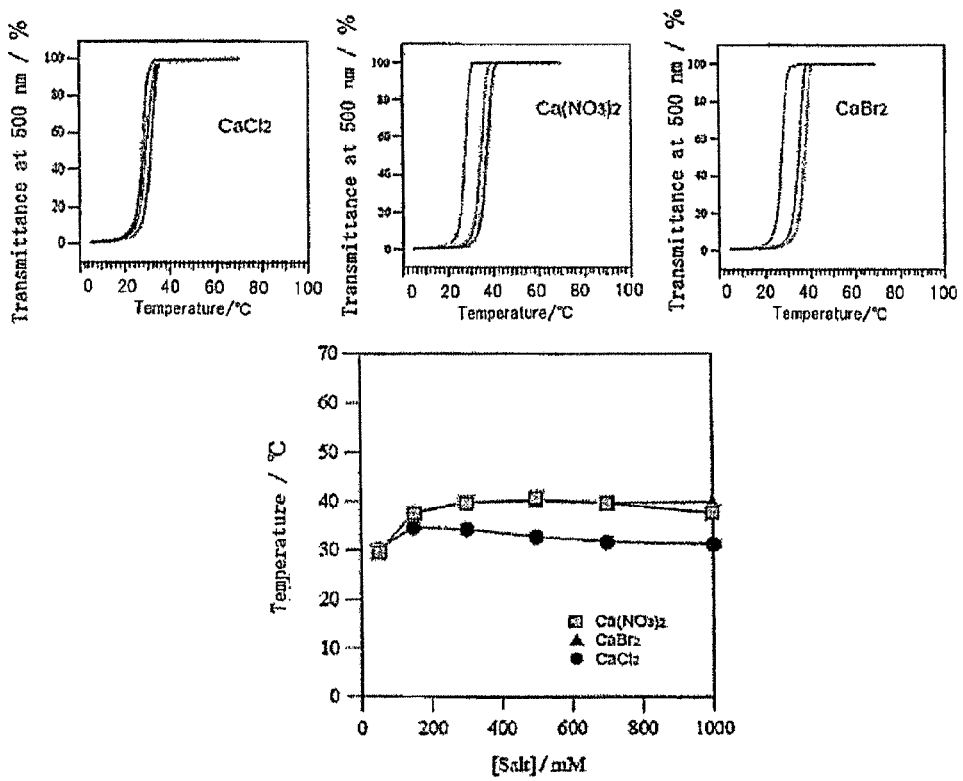
FIG. 14 shows the influence of the salt concentration on the phase transition temperature (° C.) of the succinylated carbamoylated polyallylamine (Suc-Carb-PAA-15K 87) prepared in Production Example 3 (Experiment Example 8).

FIG. 14 and Table 7 show the results. FIG. 14 (upper) shows the relationship between the solution temperature (5 to 70° C.) and the transmittance (%) of the solution. FIG. 14 (lower) shows the relationship between the salt concentration and the phase transition temperature.

TABLE 7

| Salt concentration: mM | Phase transition temperature (° C.) | | |
| --- | --- | --- | --- |
| | CaCl$_2$ | Ca(NO$_3$)$_2$ | CaBr$_2$ |
| 50 | 30.2 | 29.7 | 29.6 |
| 150 | 34.6 | 37.4 | 37.6 |
| 300 | 34.2 | 39.8 | 39.8 |
| 500 | 32.7 | 40.5 | 40.3 |
| 700 | 31.6 | 39.5 | 39.4 |
| 1000 | 31.2 | 37.5 | 38.1 |

As is clear from the table and figures, the succinylated CPA was insoluble in the aqueous solutions of 50 to 1,000 mM salts (CaCl$_2$, Ca(NO$_3$)$_2$, and CaBr$_2$) in the temperature range lower than about 30° C. to 40° C. (phase transition temperature) and soluble in the temperature range higher than the phase transition temperature. That is, it was confirmed that the succinylated CPA was a positive (upper critical solution temperature-type) thermoresponsive polymer compound.

Further, as is clear from FIG. 14 (lower), the phase transition temperature (° C.) of the succinylated CPA tended to increase in the salt concentration range of 50 to 150 mM as the salt concentration increased. The results reveal that even when, for example, the pH or temperature of the system cannot be changed, the thermoresponsive separation material comprising the succinylated CPA as an active ingredient can induce phase separation by changing the salt concentration. For example, there is a method of allowing the thermoresponsive separation material to capture an object to be separated under conditions of low salt concentration, and then adding a salt to the system to induce phase separation (separation).
(2) Evaluation of pH Dependence The concentration of the succinylated CPA was adjusted to 1 mg/mL, and the phase transition temperature (° C.) was measured while the pH was changed in the range of 4.5 to 10.5. More specifically, the succinylated CPA was dissolved in biological buffers, which had been adjusted to a pH of 4.5 to 10.5 (see the following), to a concentration of 1 mg/mL. While the solution temperature was reduced from 70° C. to 5°

C. at a rate of 1° C./min, the absorbance at 500 nm was measured by a UV-VIS spectrophotometer (absorptiometer). The phase transition temperature (° C.) was calculated from the measured absorbance according to the method of Experiment Example 2.

Figure 15:
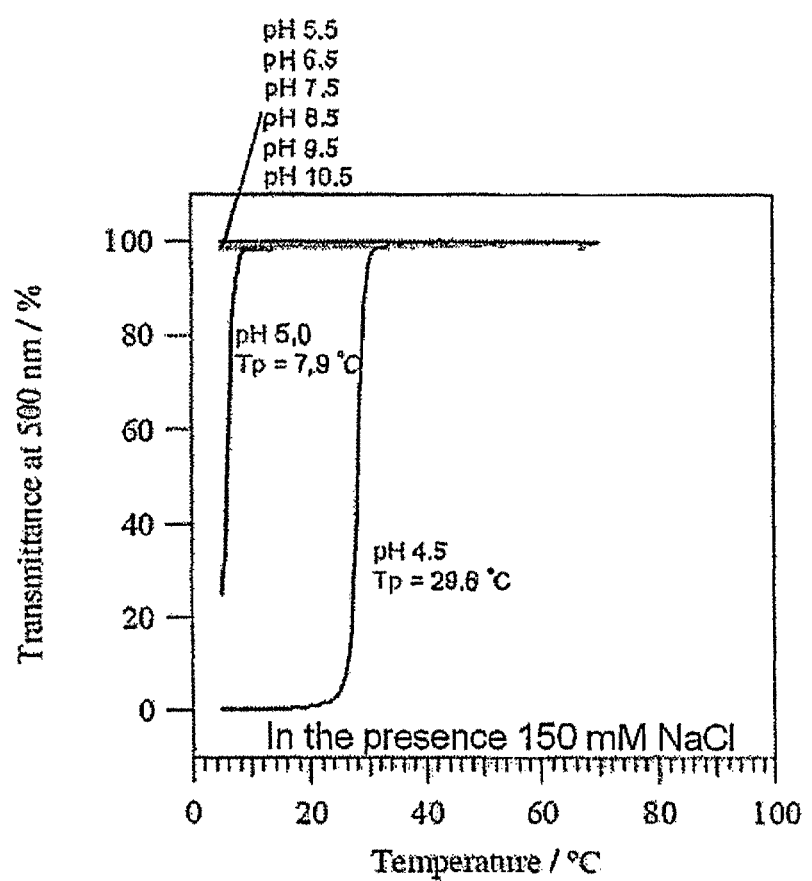
FIG. 15 shows the influence of the pH on the phase transition temperature (° C.) of the succinylated carbamoylated polyallylamine (Suc-Carb-PAA-15K 87) prepared in Production Example 3. The horizontal axis represents the temperature (° C.), and the vertical axis represents the transmittance (%) at 500 nm.

Buffers pH 4.5: 10 mM cacodylic acid+150 mM NaCl
pH 5.5 and 6.5: 10 mM MES-NaOH+150 mM NaCl
pH 7.5 and 8.5: 10 mM HEPES-NaOH+150 mM NaCl
pH 9.5 and 10.5: 10 mM boric acid-NaOH+150 mM NaCl FIG. 15 shows the results. The succinylated CPA was a positive thermoresponsive polymer compound having a phase transition temperature (° C.) in the range of 5 to 30° C. in the biological buffer containing 150 mM sodium chloride under acidic conditions of pH 4.5 to 5.5. The phase transition temperature at pH 4.5 was 7.9° C., and the phase transition temperature at pH 5.5 was 29.6° C.

The results demonstrate that even when, for example, the temperature of the system cannot be changed, the thermoresponsive separation material of the present invention can induce phase separation by changing the pH. Some sites in vivo undergo pH changes; in particular, for example, the vicinity of cancerous tissue is acidic. Accordingly, phase transition behavior presumably occurs depending on the pH environment of the tissue, and the thermoresponsive separation material of the present invention is expected to be usable for sensing.

The invention claimed is:

1. A temperature-, pH- or salt-concentration-sensitive separation material comprising, as an active ingredient, a thermoresponsive polymer compound as set forth by formula (I) or an addition salt thereof;

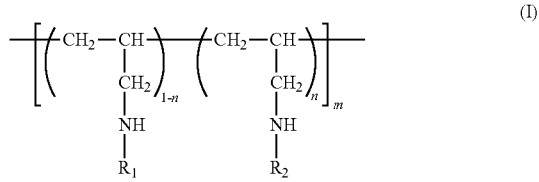

wherein m represents an integer of 10 or more, n represents a number satisfying $0.4 \leq n \leq 1$, $R_1$ represents hydrogen or a substituent as set forth by formula (1), and $R_2$ represents a substituent as set forth by formula (2):

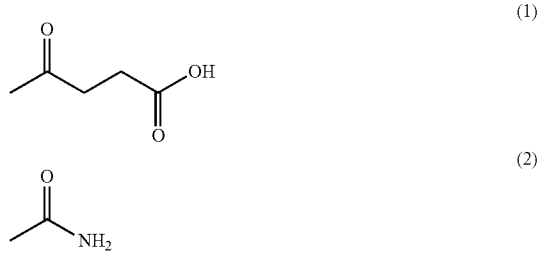

the thermoresponsive polymer compound having a phase transition temperature in the range of 5 to 65° C. in an aqueous solution with a salt concentration of at least 1 mM and a pH in the range of 3 to 10.5; and forming an insoluble phase at a temperature lower than the phase transition temperature and forming a dissolved phase at a temperature higher than the phase transition temperature.

2. The temperature-, pH- or salt-concentration-sensitive separation material according to claim 1, wherein the thermoresponsive polymer compound (I) comprises a ligand binding, via a linker if necessary, to a part of the monomers constituting the thermoresponsive polymer compound (I).

3. The temperature-, pH- or salt-concentration-sensitive separation material according to claim 2, wherein the thermoresponsive polymer compound (I) comprises a ligand binding via a linker to a part of the monomers constituting the thermoresponsive polymer compound (I), wherein the ligand is biotin or imino biotin, and the linker is an alkylene group.

4. The temperature-, pH- or salt-concentration-sensitive separation material according to claim 1, which contains an anionic substance or a cationic substance.

5. The temperature-, pH- or salt-concentration-sensitive separation material according to claim 4, wherein the anionic substance is an anionic dye and the cationic substance is a cationic dye.

6. A drug release agent comprising the temperature-, pH- or salt-concentration-sensitive separation material of claim 1 in combination with a drug.

7. A succinylated carbamoylated polyallylamine as set forth by formula (V) or an addition salt thereof:

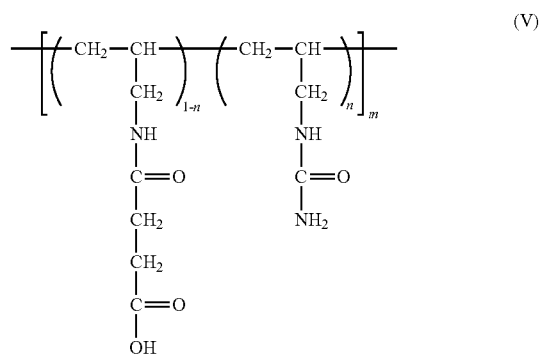

wherein m represents an integer of 10 or more, and n represents a number satisfying $0.4 \leq n \leq 1$.

8. A method for producing the succinylated carbamoylated polyallylamine according to claim 7 or the salt thereof as set forth by Formula (V) comprising:

reacting a succinic anhydride with a carbamoylated polyallylamine Formula (IV) or an addition salt thereof:

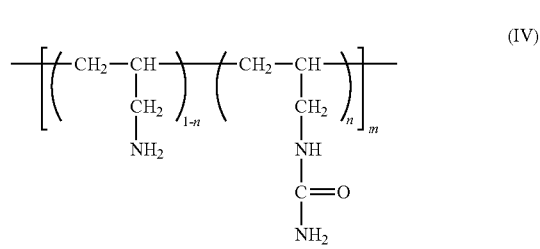

wherein m represents an integer of 10 or more, and n represents a number satisfying $0.4 \leq n \leq 1$.

9. The temperature-, pH- or salt-concentration-sensitive separation material according to claim 2, which contains an anionic substance or a cationic substance.

10. A drug release agent comprising the temperature-, pH- or salt-concentration-sensitive separation material of claim 2 in combination with a drug.

* * * * *